(12) United States Patent
Favalli

(10) Patent No.: US 11,987,844 B2
(45) Date of Patent: May 21, 2024

(54) USE OF CFDNA FRAGMENTS AS BIOMARKERS IN PATIENTS AFTER ORGAN TRANSPLANTATION

(71) Applicant: 4BASES SA, Manno (CH)

(72) Inventor: Valentina Favalli, Pavia (IT)

(73) Assignee: 4BASES SA, Manno (CH)

(*) Notice: Subject to any disclaimer, the term of this patent is extended or adjusted under 35 U.S.C. 154(b) by 368 days.

(21) Appl. No.: 16/963,355

(22) PCT Filed: Jan. 29, 2019

(86) PCT No.: PCT/EP2019/052054
§ 371 (c)(1),
(2) Date: Jul. 20, 2020

(87) PCT Pub. No.: WO2019/149673
PCT Pub. Date: Aug. 8, 2019

(65) Prior Publication Data
US 2021/0062264 A1 Mar. 4, 2021

(30) Foreign Application Priority Data
Jan. 30, 2018 (EP) .................................. 18154208

(51) Int. Cl.
*C12Q 1/68* (2018.01)
*C12P 19/34* (2006.01)
*C12Q 1/6883* (2018.01)
*G06N 20/00* (2019.01)

(52) U.S. Cl.
CPC ........... *C12Q 1/6883* (2013.01); *G06N 20/00* (2019.01); *C12Q 2600/156* (2013.01)

(58) Field of Classification Search
CPC ......................... C12Q 1/6883; C12Q 2600/156
See application file for complete search history.

(56) References Cited

U.S. PATENT DOCUMENTS

| | | | | |
|---|---|---|---|---|
| 2015/0232929 A1* | 8/2015 | Stephens | .............. | C12Q 1/6827 506/4 |
| 2016/0145682 A1* | 5/2016 | Woodward | ........... | C12Q 1/6883 506/4 |

FOREIGN PATENT DOCUMENTS

| | | |
|---|---|---|
| EP | 3285193 | 2/2018 |
| WO | WO2012115851 | 8/2012 |
| WO | WO2013159035 | 10/2013 |
| WO | WO2014194113 | 12/2014 |
| WO | WO2015069933 | 5/2015 |
| WO | WO2015138997 | 9/2015 |
| WO | WO2016167408 | 10/2016 |

OTHER PUBLICATIONS

Matthew J Hayden, et al "Multiplex-Ready PCR: A new method for multiplexed SSR and SNP genotyping" BMC Genomics 2008, 9: 80 (Year: 2008).*
Submitted SNP(ss) Details: ss10967711; RefSNP(rs#) rs1005533. Submitted Jun. 30, 2003. Printed from https://www.ncbi.nlm.nih.gov/projects/SNP (Year: 2003).*
Submitted SNP(ss) Details: ss208682621; RefSNP(rs#) rs10092491. Submitted Mar. 15, 2010. Printed from https://www.ncbi.nlm.nih.gov/projects/SNP (Year: 2010).*
Beck, Julia, et al., "Digital droplet PCR for rapid quantification of donor DNA in the circulation of transplant recipients as a potential universal biomarker of graft injury", Clinical Chemistry, 59:12, 2013, pp. 1732-1741.
Borsting, Claus, et al., "Validation of a single nucleotide polymorphism (SNP) typing assay with 49 SNPs for forensic genetic testing in a laboratory accredited according to the ISO 17025 standard", Forensic Science International; Genetics, 4, 2009, pp. 34-42.
Costanzo, Maria, Rosa, "The international society of heart and lung transplantation guidelines for the care of heart transplant recipients", The Journal of Heart and Lung Transplantation, vol. 29, No. 8, Aug. 2010, pp. 914-956.
De Vlaminck, Iwijn, et al., "Circulating cell-free DNA enables noninvasive diagnosis of heart transplant rejection". Science Translational Medicine, vol. 6, Issue 241, 241ra77, Jun. 18, 2014, pp. 1-8.
Deckers, Jaap, W., et al., "Complications of transvenous right ventricular endomyocardial biopsy in adult patients with cardiomyopathy: a seven-year survey of 546 consecutive diagnostic procedures in a tertiary referral center", JACC, vol. 19, No. 1, Jan. 1992, pp. 43-47.
Gordon, Paul, M.K., et al., "An algorithm measuring donor cell-free DNA in plasma of cellular and solid organ transplant recipients that does not require donor or recipient genotyping", Frontiers in Cardiovascular Medicine, vol. 3, Article 33, Sep. 2016, pp. 1-10.
Grskovic, Marica, et al., "Validation of a clinical-grade assay to measure donor-derived cell-free DNA in solid organ transplant recipients", The Journal of Molecular Diagnostics, vol. 18, No. 6. Nov. 2016, pp. 891-902.
Kidd, Kenneth, K., et al., "Expanding data and resources for forensic use of SNPs in individual identification", Forensic Science International: Genetics, 6, 2012, pp. 646-652.
Miller, Christopher, A., et al., "Non-invasive approaches for the diagnosis of acute cardiac allograft rejection", Heart, 99, 2013, pp. 445-453.
Oellerich, Michael, et al., "Use of graft-derived cell-free DNA as an organ integrity biomarker to reexamine effective tacrolimus trough concentrations after liver transplantation", Ther Drug Monit, Vo. 36, No. 2, Apr. 2014, pp. 136-140.
Pakstis, Andrew, J., et al., "SNPs for a universal individual identification panel", Hum Genet, 127, 2010, pp. 315-324.
Pophal, Stephen, G., et al., "Complications of endomyocardial biopsy in children", Journal of the American College of Cardiology, vol. 34, No. 7, 1999, pp. 2105-2010.
Saraiva, F., et al., "Complications of endomyocardial biopsy in heart transplant patients: a retrospective study of 2117 consecutive procedures", Transplantation Proceedings, 43, 2011, pp. 1908-1912.

(Continued)

*Primary Examiner* — Stephen T Kapushoc
(74) *Attorney, Agent, or Firm* — HUESCHEN AND SAGE

(57) ABSTRACT

The present invention provides methods for detecting donor cell-free DNA in the circulation of an organ transplant recipient for the early identification of transplant rejection.

10 Claims, 6 Drawing Sheets

Specification includes a Sequence Listing.

(56) References Cited

OTHER PUBLICATIONS

Schütz, Ekkehard, et al., "Graft-derived cell-free DNA, a noninvasive early rejection and graft damage marker in liver transplantation: a prospective, observational, multicenter cohort study", PLOS Medicine, 14(4): e1002286, Apr. 25, 2017, pp. 1-19.

Sigdel, Tara, K., et al., "A rapid noninvasive assay for the detection of renal transplant injury", Transplantation, 96(1), Jul. 15, 2013, pp. 97-101.

Snyder, Thomas, M. et al, "Universal noninvasive detection of solid organ transplant rejection", PNAS, vol. 108., No. 15, Apr. 12, 2011, pp. 6229-6234.

Stehlik, J., et al., "Utility of long-term survelillance endomyocardial biopsy: a multi-institutional analysis", The Journal of Heart and Lung Transplantation, vol. 25, No. 12. 2006, pp. 1402-1409.

Stewart, Susan, et al., "Revision of the 1990 working formulation for the standardization of nomenclature in the diagnosis of heart rejection", The Journal of Heart and Lung Transplantation, vol. 24, No. 11, 2005, pp. 1710-1720.

\* cited by examiner

SEQUENCE LISTING

<160> NUMBER OF SEQ ID NOS: 270

<210> SEQ ID NO 1
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
    /organism="Homo sapiens"

<400> SEQUENCE: 1 tcagaccta gtcccagctg ggtgag                                        26

```
<210> SEQ ID NO 2
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 2
ttgggggcat ctgaaacact cacacac                                27

<210> SEQ ID NO 3
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 3
ttccctggtc ttgccctgc act                                     23

<210> SEQ ID NO 4
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 4
caatgctcac agagatctcc cagatca                                27

<210> SEQ ID NO 5
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 5
gaatccacag ctgcagaaaa ccaaatg                                27

<210> SEQ ID NO 6
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 6
tctatcacag aattatttat atatggccca                             30

<210> SEQ ID NO 7
<211> LENGTH: 30
```

```
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 7
cgacatggga aatgtcagat cataagacat                                       30

<210> SEQ ID NO 8
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 8
ctttggattc taaagtggat ctaataacag                                       30

<210> SEQ ID NO 9
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 9
agcatttaaa cagctatgaa tccacct                                          27

<210> SEQ ID NO 10
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 10
tttcaacatg cccttaggga attcatg                                          27

<210> SEQ ID NO 11
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 11
caataacgtc cagggagtga aaaatcc                                          27

<210> SEQ ID NO 12
<211> LENGTH: 25
<212> TYPE: DNA
<213> ORGANISM: Homo sapiens
<220> FEATURE:
<221> NAME/KEY: source
```

```
<222> LOCATION: 1..25
<223> OTHER INFORMATION: /mol_type="other DNA"
      /organism="Homo sapiens"

<400> SEQUENCE: 12
tacatgttcc acttcccatg tgctc                                           25

<210> SEQ ID NO 13
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 13
tcaccagccc cagcaagggc atggga                                          27

<210> SEQ ID NO 14
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 14
aagaccacag gtcagggagg cat                                             23

<210> SEQ ID NO 15
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 15
ccaagcccta tgccaaggat ataacaat                                        28

<210> SEQ ID NO 16
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 16
atgggctcac ggaagaagaa cacaaag                                         27

<210> SEQ ID NO 17
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"
```

```
<400> SEQUENCE: 17
gagcatactt gaaagcagtg attatatc                                      28

<210> SEQ ID NO 18
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 18
agacaaaaac tggaaaatat ttgaattacc                                    30

<210> SEQ ID NO 19
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 19
aagggtactc attaaccaag tgtttta                                       27

<210> SEQ ID NO 20
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 20
tctgaagcat gtttcgcaaa gtgcag                                        26

<210> SEQ ID NO 21
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 21
gggaactcct aatacagtaa aacctct                                       27

<210> SEQ ID NO 22
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 22
cactagattt aagttctttc ctgatgtg                                      28
```

```
<210> SEQ ID NO 23
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 23
gttctcccaa atttacattg ccactga                                        27

<210> SEQ ID NO 24
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 24
caaggatacc aaacctgcag gcataaa                                        27

<210> SEQ ID NO 25
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
      /organism="Homo sapiens"

<400> SEQUENCE: 25
atgccaggcc agccacagag tgcc                                           24

<210> SEQ ID NO 26
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 26
cagaaccttg aaccagtgca tggtta                                         26

<210> SEQ ID NO 27
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 27
atcactgtcc atcacgacac cgagtg                                         26

<210> SEQ ID NO 28
<211> LENGTH: 21
<212> TYPE: DNA
```

-continued

```
<213> ORGANISM: Homo sapiens
<220> FEATURE:
<221> NAME/KEY: source
<222> LOCATION: 1..21
<223> OTHER INFORMATION: /mol_type="other DNA"
      /organism="Homo sapiens"

<400> SEQUENCE: 28
ccctccagtg ttttgggtgg g                                        21

<210> SEQ ID NO 29
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 29
tatgaacccc cagcatgggg cggggc                                   26

<210> SEQ ID NO 30
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 30
tctctctggg atcatgtgag gcgggaa                                  27

<210> SEQ ID NO 31
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 31
gggctgaaag atgatggcag agc                                      23

<210> SEQ ID NO 32
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="other DNA"
      /organism="Homo sapiens"

<400> SEQUENCE: 32
cctcaccacc agctctgtga ca                                       22

<210> SEQ ID NO 33
<211> LENGTH: 27
<212> TYPE: DNA
<213> ORGANISM: Homo sapiens
<220> FEATURE:
<221> NAME/KEY: source
<222> LOCATION: 1..27
```

```
<223> OTHER INFORMATION: /mol_type="other DNA"
      /organism="Homo sapiens"

<400> SEQUENCE: 33
ggacaggtgc ttggatgtca gggtgaa                                              27

<210> SEQ ID NO 34
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 34
gtccaaccaa caaggatgtg gaggaat                                              27

<210> SEQ ID NO 35
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 35
ctggggatga actctctttg gagttt                                               26

<210> SEQ ID NO 36
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 36
tttggaaggg tttttcgtct tgtttag                                              27

<210> SEQ ID NO 37
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 37 tcattttac catttaacag ctctgatg                                              28

<210> SEQ ID NO 38
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 38
```

-continued agaatcacag actcttacag gtcctag 27

<210> SEQ ID NO 39
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
    /organism="Homo sapiens"

<400> SEQUENCE: 39
tgagttttta cctacctttc ttgcaca 27

<210> SEQ ID NO 40
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
    /organism="Homo sapiens"

<400> SEQUENCE: 40
agtgccttaa caacagcaaa atctctc 27

<210> SEQ ID NO 41
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
    /organism="Homo sapiens"

<400> SEQUENCE: 41
taccatgtct ccccaggctc tccg 24

<210> SEQ ID NO 42
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
    /organism="Homo sapiens"

<400> SEQUENCE: 42
ctccttaaaa catagtctga tacttatcg 29

<210> SEQ ID NO 43
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
    /organism="Homo sapiens"

<400> SEQUENCE: 43
aggtgggaca aaggcaggaa gaaagta 27

```
<210> SEQ ID NO 44
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 44
ggcacactta attttaacag aaggagg                                27

<210> SEQ ID NO 45
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 45
cacagagaca tgaggcattt tcatgga                                27

<210> SEQ ID NO 46
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 46
gtttcagtcc acagcagaaa aagactc                                27

<210> SEQ ID NO 47
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 47
gaggtacagc tcccactgcc tctgagt                                27

<210> SEQ ID NO 48
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 48 ttgcccttttt cattggacaa ctaaaaa                               27

<210> SEQ ID NO 49
<211> LENGTH: 27
<212> TYPE: DNA
<213> ORGANISM: Homo sapiens
```

```
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 49
ctactgcacg tggatgatat ggtttct                                27

<210> SEQ ID NO 50
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 50
atgacattca tcaaaatgaa attgcca                                27

<210> SEQ ID NO 51
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 51
aacaatacat acctgcaccc tgccctt                                27

<210> SEQ ID NO 52
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 52
gagagtgaca tctaggttgt catctga                                27

<210> SEQ ID NO 53
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 53
ttgaaaaagc atcagattaa aacaaagat                              29

<210> SEQ ID NO 54
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
```

/organism="Homo sapiens"

<400> SEQUENCE: 54
agttcagcaa acactatgca ggataaa                                          27

<210> SEQ ID NO 55
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 55
cctttctgtt ttgtccatct gaaattc                                          27

<210> SEQ ID NO 56
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 56
taatgaaaca tctgagtact ttttaggtc                                        29

<210> SEQ ID NO 57
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 57
gtgtcttaaa acccatgatt ttcttgtg                                         28

<210> SEQ ID NO 58
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 58
attttccttc ttcttgcagc tttgagt                                          27

<210> SEQ ID NO 59
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 59
aggcctccag tggctctgaa attctca                                27

<210> SEQ ID NO 60
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 60
tcttcagacc tgtaatgggg ctatttg                                27

<210> SEQ ID NO 61
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 61
cagaccactt caccctctgt acttta                                 26

<210> SEQ ID NO 62
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 62
gtttgagaca caattccccc agg                                    23

<210> SEQ ID NO 63
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 63
cccaaattca gcttgggaag tcaaa                                  25

<210> SEQ ID NO 64
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 64
agattttgct gtgaaagtga gtgtctg                                27

<210> SEQ ID NO 65

```
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 65
gtcacagctt cgctttgcta ctctt                                          25

<210> SEQ ID NO 66
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="other DNA"
      /organism="Homo sapiens"

<400> SEQUENCE: 66
gacggcaggt gggggtcacc                                                20

<210> SEQ ID NO 67
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 67
cctccagacc tgaaagatgg aggcttt                                        27

<210> SEQ ID NO 68
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 68 gtgtcccccct caatcccctc tccattt                                       27

<210> SEQ ID NO 69
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 69
tgtagaattt gattaaagtg tcttctgga                                      29

<210> SEQ ID NO 70
<211> LENGTH: 29
<212> TYPE: DNA
<213> ORGANISM: Homo sapiens
<220> FEATURE:
```

```
<221> NAME/KEY: source
<222> LOCATION: 1..29
<223> OTHER INFORMATION: /mol_type="other DNA"
      /organism="Homo sapiens"

<400> SEQUENCE: 70
gctctgtaac atcctaaggg atttttgct                              29

<210> SEQ ID NO 71
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 71
gccgacttat tagacggaca gcatttt                                27

<210> SEQ ID NO 72
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 72
aatggaatgt tgcagcttga acataat                                27

<210> SEQ ID NO 73
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 73
ctggaacaca tcaaaaacca ccatctc                                27

<210> SEQ ID NO 74
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 74
gcctcaccca aaggcagaca tag                                    23

<210> SEQ ID NO 75
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"
```

```
<400> SEQUENCE: 75
atacttggct gtctgggagc ctgtag                                          26

<210> SEQ ID NO 76
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 76
atgggcatac atgcatacac atgtgc                                          26

<210> SEQ ID NO 77
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 77
atgttggtgg aagggactga gaagcct                                         27

<210> SEQ ID NO 78
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 78
tttctgtgct gagcatttta tatgtgc                                         27

<210> SEQ ID NO 79
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 79
tcacagtgat ccatacacta aaacaag                                         27

<210> SEQ ID NO 80
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 80
agacttttgt taaattatca tcaaggagat                                      30
```

<210> SEQ ID NO 81
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 81
ccagagacct gttctctgtc cattatt                                              27

<210> SEQ ID NO 82
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 82
aattgcagct gagagaaaac agtagta                                              27

<210> SEQ ID NO 83
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 83
gatctatgga agtgctgaga agggaag                                              27

<210> SEQ ID NO 84
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 84
cgctcactcc cctacaaatg tcaacaa                                              27

<210> SEQ ID NO 85
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
      /organism="Homo sapiens"

<400> SEQUENCE: 85
tgggtgagac aatgcacaga actg                                                 24

<210> SEQ ID NO 86
<211> LENGTH: 26

```
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 86
aaaaagcact gggatcctca ctttgg                                          26

<210> SEQ ID NO 87
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 87
gatgctatcg ctggctatta ggtgatc                                         27

<210> SEQ ID NO 88
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 88
atacaggtag agagtgatga agccaag                                         27

<210> SEQ ID NO 89
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 89
agagagattg attatgttgg gatgggg                                         27

<210> SEQ ID NO 90
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 90
tgcagtttgc tgagtttcac caaatc                                          26

<210> SEQ ID NO 91
<211> LENGTH: 27
<212> TYPE: DNA
<213> ORGANISM: Homo sapiens
<220> FEATURE:
<221> NAME/KEY: source
```

```
<222> LOCATION: 1..27
<223> OTHER INFORMATION: /mol_type="other DNA"
      /organism="Homo sapiens"

<400> SEQUENCE: 91
tgatccacat tgtatggttt ttaggca                                          27

<210> SEQ ID NO 92
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 92
gtgcttatta gatgtttgtg ctcacaa                                          27

<210> SEQ ID NO 93
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 93
ttgatgtttc tgtgtgttga gtggggg                                          27

<210> SEQ ID NO 94
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 94
ggatctggct gttccttagt tcatcat                                          27

<210> SEQ ID NO 95
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 95
agagcgcttg tctgaatgga gac                                              23

<210> SEQ ID NO 96
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"
```

-continued

```
<400> SEQUENCE: 96
cattttaaag aaaagaggag ctgggtg                                           27

<210> SEQ ID NO 97
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 97
cagtgcaaga caagcgattg aaagaag                                           27

<210> SEQ ID NO 98
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 98
aagggacaag gaaagagtgc tccttc                                            26

<210> SEQ ID NO 99
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 99
cccagtctcc aaaccgctgt aatattt                                           27

<210> SEQ ID NO 100
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
      /organism="Homo sapiens"

<400> SEQUENCE: 100
gcccttgtgc acatagatgc aaag                                              24

<210> SEQ ID NO 101
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 101
atgagcaaga gttccaacgt tccatg                                            26
```

```
<210> SEQ ID NO 102
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 102
tgaatccaaa ggtggattct ctaaggc                                27

<210> SEQ ID NO 103
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 103
aaattgaatc atagcttgtg ttggtcagg                              29

<210> SEQ ID NO 104
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 104
ttctcaaagg aaagaaaaat atcagttca                              29

<210> SEQ ID NO 105
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 105
cagaccaact tggctttaac agatgca                                27

<210> SEQ ID NO 106
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 106
cacaaaagaa ctggcattcc agaact                                 26

<210> SEQ ID NO 107
<211> LENGTH: 29
<212> TYPE: DNA
```

```
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 107
tgtatcctta cctttaagac ttttcctat                                    29

<210> SEQ ID NO 108
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 108
atgcaaatat cagttttgat gaagcaa                                      27

<210> SEQ ID NO 109
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 109
tgatcgttca tagacaatag atacataca                                    29

<210> SEQ ID NO 110
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
      /organism="Homo sapiens"

<400> SEQUENCE: 110
ggctttcaag cgtttctgca atga                                         24

<210> SEQ ID NO 111
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 111
cgttctgtat aggcaccata tagcact                                      27

<210> SEQ ID NO 112
<211> LENGTH: 24
<212> TYPE: DNA
<213> ORGANISM: Homo sapiens
<220> FEATURE:
<221> NAME/KEY: source
<222> LOCATION: 1..24
```

```
<223> OTHER INFORMATION: /mol_type="other DNA"
      /organism="Homo sapiens"

<400> SEQUENCE: 112
acggattgaa tgaagcagcg gtct                                      24

<210> SEQ ID NO 113
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 113
agacttttgg cttaaatcaa tgggtct                                   27

<210> SEQ ID NO 114
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 114
tcatgggagt ttctgatgtc actaagg                                   27

<210> SEQ ID NO 115
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 115
accactcaca tgtcaaataa aataactg                                  28

<210> SEQ ID NO 116
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 116
ctcccactga acttcataaa aacaaaaga                                 29

<210> SEQ ID NO 117
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 117
```
ttatcccttt cctgtctggg ctgaatc                                    27

<210> SEQ ID NO 118
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="other DNA"
      /organism="Homo sapiens"

<400> SEQUENCE: 118
gggggttgga gtggggcgga                                            20

<210> SEQ ID NO 119
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 119
gtgcacattc taagaactgg tgattct                                    27

<210> SEQ ID NO 120
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 120
ccttcaggga tttccagcag tgg                                        23

<210> SEQ ID NO 121
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 121
tttggagctt ggtgatgagt ggaggct                                    27

<210> SEQ ID NO 122
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 122
agacaaccat gagcagaatg ctggta                                     26

```
<210> SEQ ID NO 123
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 123
ttctgttgtg gctcgtcttc ctgagc                                26

<210> SEQ ID NO 124
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="other DNA"
      /organism="Homo sapiens"

<400> SEQUENCE: 124
gcctctgaga gggtagggac a                                     21

<210> SEQ ID NO 125
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 125
atccaatgct cagggagac attagct                                27

<210> SEQ ID NO 126
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 126
tcctatctaa ttcttctaat ttctcgtcaa                            30

<210> SEQ ID NO 127
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 127
ccagcatctg ttgttttaac tttcttt                               27

<210> SEQ ID NO 128
<211> LENGTH: 28
<212> TYPE: DNA
<213> ORGANISM: Homo sapiens
```

```
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 128
agaagtatct gttcatgtat tttgctga                                          28

<210> SEQ ID NO 129
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 129
caaagaactg acccttgcag agaact                                            26

<210> SEQ ID NO 130
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 130
gattctagca agagaatgca ggtgct                                            26

<210> SEQ ID NO 131
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 131
actccagaag ctactgggat attaatta                                          28

<210> SEQ ID NO 132
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 132
gttcattaag aaaacctgtg acaaacat                                          28

<210> SEQ ID NO 133
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
```

/organism="Homo sapiens"

<400> SEQUENCE: 133
tctctaaact tccttgatat taactactga                                30

<210> SEQ ID NO 134
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 134
atacttacca gactgcctgc ttcttag                                   27

<210> SEQ ID NO 135
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 135
gaacatagtt caaggaggta cagcctc                                   27

<210> SEQ ID NO 136
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 136
tgcagccttc ctatttaccg aaagc                                     25

<210> SEQ ID NO 137
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 137
cagtctgtgt agccaacaca cactaat                                   27

<210> SEQ ID NO 138
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 138
ccaatttccc agcctacatc agctatt                                27

<210> SEQ ID NO 139
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 139
taaacctatt ccactaactt caggaac                                27

<210> SEQ ID NO 140
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 140
agtgtacctg cagaactgta gagaatc                                27

<210> SEQ ID NO 141
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 141
cagaagtgga atcacaaaag gaaaaca                                27

<210> SEQ ID NO 142
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 142
aaattgtagg tgtgtaagtg catctct                                27

<210> SEQ ID NO 143
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 143
ctcctacaca caggcttcag gttac                                  25

<210> SEQ ID NO 144

```
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 144
atttttccca gtcccttta c caaaaa                                              26

<210> SEQ ID NO 145
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 145
tgtgcctgtg cacacacacg tttgg                                                25

<210> SEQ ID NO 146
<211> LENGTH: 20
<212> TYPE: DNA
<213> ORGANISM: Homo sapiens
<220> FEATURE:
<221> NAME/KEY: source
<222> LOCATION: 1..20
<223> OTHER INFORMATION: /mol_type="other DNA"
      /organism="Homo sapiens"

<400> SEQUENCE: 146
gccaggagcg cagctcacgc                                                      20

<210> SEQ ID NO 147
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 147
cagccgaaga atccagccct tgt                                                  23

<210> SEQ ID NO 148
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 148
gacctttccc cgctcagagc tccttca                                              27

<210> SEQ ID NO 149
<211> LENGTH: 28
<212> TYPE: DNA
<213> ORGANISM: Homo sapiens
<220> FEATURE:
```

```
<221> NAME/KEY: source
<222> LOCATION: 1..28
<223> OTHER INFORMATION: /mol_type="other DNA"
      /organism="Homo sapiens"

<400> SEQUENCE: 149
aaagaggggt gttctggtgg cttctctt                                            28

<210> SEQ ID NO 150
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 150
cacctcttat cagtacgcag gcaaa                                               25

<210> SEQ ID NO 151
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 151
gtgatacatg agagagatac ataaggg                                             27

<210> SEQ ID NO 152
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 152
tcctccctga aaattatagc aggtct                                              26

<210> SEQ ID NO 153
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 153
acgggtgaaa gctgatatct tgacct                                              26

<210> SEQ ID NO 154
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"
```

<400> SEQUENCE: 154
gtaatttgcc atcactttca gtggcaa    27

<210> SEQ ID NO 155
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 155
tcaaaaacaa agaaacatgg gatgaac    27

<210> SEQ ID NO 156
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 156
cagatccatc attgccagta gacaaac    27

<210> SEQ ID NO 157
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 157
caagaggagt caaggcattt gacca    25

<210> SEQ ID NO 158
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="other DNA"
      /organism="Homo sapiens"

<400> SEQUENCE: 158
ttggcattca gcggccccca ga    22

<210> SEQ ID NO 159
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 159
cattcaccat ttgatagcca tttgggt    27

<210> SEQ ID NO 160
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 160
tgtaagtaat tataccattt tacactccca                                       30

<210> SEQ ID NO 161
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 161
gttttgatca ccaaccactt gcagtt                                           26

<210> SEQ ID NO 162
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 162
gcctggacaa catgatgtct ctatattaaa                                       30

<210> SEQ ID NO 163
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 163
cacctggcct acaattcaaa ttaatgt                                          27

<210> SEQ ID NO 164
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 164
agtttgaatc agaaataaga tgtgaatga                                        29

<210> SEQ ID NO 165
<211> LENGTH: 24

```
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
      /organism="Homo sapiens"

<400> SEQUENCE: 165
actcctgggg atacaagagc ttcc                                              24

<210> SEQ ID NO 166
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 166
ttattgtcag cgttgtttaa attctgg                                           27

<210> SEQ ID NO 167
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="other DNA"
      /organism="Homo sapiens"

<400> SEQUENCE: 167
gaggaagccg ttgctggtct c                                                 21

<210> SEQ ID NO 168
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 168
atctccaagc tcagctcagc ccaaga                                            26

<210> SEQ ID NO 169
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
      /organism="Homo sapiens"

<400> SEQUENCE: 169
aatctgagct cgaggtagca ggaa                                              24

<210> SEQ ID NO 170
<211> LENGTH: 21
<212> TYPE: DNA
<213> ORGANISM: Homo sapiens
<220> FEATURE:
<221> NAME/KEY: source
```

```
<222> LOCATION: 1..21
<223> OTHER INFORMATION: /mol_type="other DNA"
      /organism="Homo sapiens"

<400> SEQUENCE: 170
cagggagggc tttggtgtct g                                             21

<210> SEQ ID NO 171
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 171
ggcctgtgct ttcactggga tgcaaat                                       27

<210> SEQ ID NO 172
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 172
gtggggaaaa gtgagtgatt cgtgtt                                        26

<210> SEQ ID NO 173
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 173
cgtgactctc atatatctgt ggaagca                                       27

<210> SEQ ID NO 174
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 174
tcagaaagaa actggtggga actcc                                         25

<210> SEQ ID NO 175
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"
```

```
<400> SEQUENCE: 175
aggcattttt ctctcatctt gtttgca                                           27

<210> SEQ ID NO 176
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 176
gggaggcaca aagaggttg atg                                                23

<210> SEQ ID NO 177
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 177
gttagaaagg agaatcagga aatagtca                                          28

<210> SEQ ID NO 178
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 178
cctctttaat ttactcaaga ctaattagcc                                        30

<210> SEQ ID NO 179
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 179
tcaaagcacc aggcatttga cct                                               23

<210> SEQ ID NO 180
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 180
gggataaatt tggcctctgt atcaacc                                           27
```

```
<210> SEQ ID NO 181
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 181
attttcatag aagtacttca tttggctag                                29

<210> SEQ ID NO 182
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 182
ttcccaacta tggtgaaaga aaatcaa                                  27

<210> SEQ ID NO 183
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 183
ttcttatgta atcgtcatcc aacaaga                                  27

<210> SEQ ID NO 184
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 184
ggagaggatg gtgtggggaa aataaaa                                  27

<210> SEQ ID NO 185
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 185
gaaatacttt ccccaacaag gcagttt                                  27

<210> SEQ ID NO 186
<211> LENGTH: 27
<212> TYPE: DNA
```

```
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 186
tgacaaaata acaagttccg tttgatt                                          27

<210> SEQ ID NO 187
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 187
cgttcaccac acagttaata cgatatgc                                         28

<210> SEQ ID NO 188
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 188
tctctagaac ctgccaaatc acttatt                                          27

<210> SEQ ID NO 189
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 189
ataaaaggat atggcaaata agctttagaa                                       30

<210> SEQ ID NO 190
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 190
gattgcttgc ccacattcca ttcaaag                                          27

<210> SEQ ID NO 191
<211> LENGTH: 27
<212> TYPE: DNA
<213> ORGANISM: Homo sapiens
<220> FEATURE:
<221> NAME/KEY: source
<222> LOCATION: 1..27
```

```
<223> OTHER INFORMATION: /mol_type="other DNA"
        /organism="Homo sapiens"

<400> SEQUENCE: 191
gattgcttgc ccacattcca ttcaaag                                          27

<210> SEQ ID NO 192
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
        /organism="Homo sapiens"

<400> SEQUENCE: 192
gattgcttgc ccacattcca ttcaaag                                          27

<210> SEQ ID NO 193
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
        /organism="Homo sapiens"

<400> SEQUENCE: 193
gattgcttgc ccacattcca ttcaaag                                          27

<210> SEQ ID NO 194
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
        /organism="Homo sapiens"

<400> SEQUENCE: 194
gattgcttgc ccacattcca ttcaaag                                          27

<210> SEQ ID NO 195
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
        /organism="Homo sapiens"

<400> SEQUENCE: 195
gattgcttgc ccacattcca ttcaaag                                          27

<210> SEQ ID NO 196
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
        /organism="Homo sapiens"

<400> SEQUENCE: 196
```
gattgcttgc ccacattcca ttcaaag                                27

<210> SEQ ID NO 197
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 197
gattgcttgc ccacattcca ttcaaag                                27

<210> SEQ ID NO 198
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 198
gattgcttgc ccacattcca ttcaaag                                27

<210> SEQ ID NO 199
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 199
gattgcttgc ccacattcca ttcaaag                                27

<210> SEQ ID NO 200
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 200
gattgcttgc ccacattcca ttcaaag                                27

<210> SEQ ID NO 201
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 201
atgattgtaa gtcgttgaag ttccgg                                 26

```
<210> SEQ ID NO 202
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 202
aaagaacata ctttggctca ttctggt                                          27

<210> SEQ ID NO 203
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 203
ctgagatccc tttgatagcg ctttcta                                          27

<210> SEQ ID NO 204
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 204
catatttcct caatataaat tctaacacgc                                       30

<210> SEQ ID NO 205
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 205
taggggttga gtccatgcca agacaa                                           26

<210> SEQ ID NO 206
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 206
accacatccc caattagagt caagaa                                           26

<210> SEQ ID NO 207
<211> LENGTH: 25
<212> TYPE: DNA
<213> ORGANISM: Homo sapiens
```

```
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 207
cttgccaaag aaaactcaag cgagg                                              25

<210> SEQ ID NO 208
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 208
gggggcactt ctgaagggga ctgtgtt                                            27

<210> SEQ ID NO 209
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 209
aaaaagaagg tcgacgccgg ctccagaagg                                         30

<210> SEQ ID NO 210
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="other DNA"
      /organism="Homo sapiens"

<400> SEQUENCE: 210
cgactagccc ggtttcccaa ga                                                 22

<210> SEQ ID NO 211
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 211
ctctccggtt ttctccaggt taggt                                              25

<210> SEQ ID NO 212
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
```

/organism="Homo sapiens"

<400> SEQUENCE: 212
gacagcaaaa catggacaaa ccctatc                27

<210> SEQ ID NO 213
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 213
ttactgtgat gtaggcactg ttccag                 26

<210> SEQ ID NO 214
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 214
agagaggtct cagggcccaa gccatc                 26

<210> SEQ ID NO 215
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 215
attgtcctcc ttgagatgtg gcttcc                 26

<210> SEQ ID NO 216
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 216
ccattacctg agaaggcatt tctaaag                27

<210> SEQ ID NO 217
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 217

```
ccggttcatt aataagacgg gacatcc                                  27

<210> SEQ ID NO 218
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 218
gggtttcatg ttatggagaa aaacaac                                  27

<210> SEQ ID NO 219
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 219
ccctttctct gttcataggc aaacaca                                  27

<210> SEQ ID NO 220
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 220
tctaactcat tcttttaac agctgcg                                   27

<210> SEQ ID NO 221
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 221
cagccaaacc atatcaagtg ctttctg                                  27

<210> SEQ ID NO 222
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 222
tgtttgtaat tgattttgtt actctttgg                                29

<210> SEQ ID NO 223
```

```
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 223
aaatgtatac attatttgct gaaaagtgc                                29

<210> SEQ ID NO 224
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 224
tgataaatgt tgaagcctac actgaag                                  27

<210> SEQ ID NO 225
<211> LENGTH: 24
<212> TYPE: DNA
<213> ORGANISM: Homo sapiens
<220> FEATURE:
<221> NAME/KEY: source
<222> LOCATION: 1..24
<223> OTHER INFORMATION: /mol_type="other DNA"
      /organism="Homo sapiens"

<400> SEQUENCE: 225
aacctctgtg ttctgagcca cgtg                                     24

<210> SEQ ID NO 226
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 226
tagctgcttc agcctggtgg tctggg                                   26

<210> SEQ ID NO 227
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 227
tccttgaggc tcttctcaca ctcagat                                  27

<210> SEQ ID NO 228
<211> LENGTH: 27
<212> TYPE: DNA
<213> ORGANISM: Homo sapiens
<220> FEATURE:
```

```
<221> NAME/KEY: source
<222> LOCATION: 1..27
<223> OTHER INFORMATION: /mol_type="other DNA"
      /organism="Homo sapiens"

<400> SEQUENCE: 228
aatatgactg gagttcatct gtgtgcc                                            27

<210> SEQ ID NO 229
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 229
tctgctatcc tgatgagaga taggt                                              25

<210> SEQ ID NO 230
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 230
tttctcaaat acacaaaaga gtttaccaa                                          29

<210> SEQ ID NO 231
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 231
tgatgctgaa ttttgtctct gttatattag                                         30

<210> SEQ ID NO 232
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 232
ttttcctctt gatccctcat attgcct                                            27

<210> SEQ ID NO 233
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"
```

<400> SEQUENCE: 233
tctctctggt tcacaaatga gcatgc                                  26

<210> SEQ ID NO 234
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 234
gctgccattt ttcttccagg aagtatc                                 27

<210> SEQ ID NO 235
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="other DNA"
      /organism="Homo sapiens"

<400> SEQUENCE: 235
actccaactc ctgccagcct t                                       21

<210> SEQ ID NO 236
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 236
ggccagcctg actaacatgg caaaat                                  26

<210> SEQ ID NO 237
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 237
gttgtttaaa cattttaaac catgagaagt                              30

<210> SEQ ID NO 238
<211> LENGTH: 22
<212> TYPE: DNA
<213> ORGANISM: Homo sapiens
<220> FEATURE:
<221> NAME/KEY: source
<222> LOCATION: 1..22
<223> OTHER INFORMATION: /mol_type="other DNA"
      /organism="Homo sapiens"

<400> SEQUENCE: 238
tgcatgatga ttcccctgcc aa                                      22

```
<210> SEQ ID NO 239
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 239
tcaaatttag tagatgtaga cagactcc                                           28

<210> SEQ ID NO 240
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 240
gactgttctc tggcttaaga tttatttagg                                         30

<210> SEQ ID NO 241
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 241
cttgtgtttt cttcaatcac ttcttatttt                                         30

<210> SEQ ID NO 242
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 242
aagtgtacaa aactccatgt accaggt                                            27

<210> SEQ ID NO 243
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 243
agaggcaacg ccaccatcat acagac                                             26

<210> SEQ ID NO 244
<211> LENGTH: 26
```

```
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 244
atggctgtcc tcctggatgg taaata                                        26

<210> SEQ ID NO 245
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 245
cgaaaaggtg aaaccagtcc tcttttg                                       27

<210> SEQ ID NO 246
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 246
agaatcgtta tcaggaactc cctgggc                                       27

<210> SEQ ID NO 247
<211> LENGTH: 30
<212> TYPE: DNA
<213> ORGANISM: Homo sapiens
<220> FEATURE:
<221> NAME/KEY: source
<222> LOCATION: 1..30
<223> OTHER INFORMATION: /mol_type="other DNA"
      /organism="Homo sapiens"

<400> SEQUENCE: 247
tataaatcac ggagtgcaga ccagtcacct                                    30

<210> SEQ ID NO 248
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 248
agggtcccgt gtgatcatca ttgtatc                                       27

<210> SEQ ID NO 249
<211> LENGTH: 27
<212> TYPE: DNA
<213> ORGANISM: Homo sapiens
<220> FEATURE:
<221> NAME/KEY: source
```

```
<222> LOCATION: 1..27
<223> OTHER INFORMATION: /mol_type="other DNA"
      /organism="Homo sapiens"

<400> SEQUENCE: 249
ctgagcccgc ccccacccag tgcaaaa                                            27

<210> SEQ ID NO 250
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 250
tctgtgaaag tttctgttct ctctctc                                            27

<210> SEQ ID NO 251
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 251
agaagcttga gcaaaggcct tgagat                                             26

<210> SEQ ID NO 252
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="other DNA"
      /organism="Homo sapiens"

<400> SEQUENCE: 252
ctaaagggca ggtgccagct g                                                  21

<210> SEQ ID NO 253
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 253
tcttctctta gaaggacact ggtcaga                                            27

<210> SEQ ID NO 254
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"
```

<400> SEQUENCE: 254
ccataataga agggtgcacg ggaattt                                27

<210> SEQ ID NO 255
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 255
gccggggact ttgactatta aatgaac                                27

<210> SEQ ID NO 256
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="other DNA"
      /organism="Homo sapiens"

<400> SEQUENCE: 256
caggtacctt cctgacgccc a                                      21

<210> SEQ ID NO 257
<211> LENGTH: 28
<212> TYPE: DNA
<213> ORGANISM: Homo sapiens
<220> FEATURE:
<221> NAME/KEY: source
<222> LOCATION: 1..28
<223> OTHER INFORMATION: /mol_type="other DNA"
      /organism="Homo sapiens"

<400> SEQUENCE: 257
gctgtttaag ggtaaagggg tagttact                               28

<210> SEQ ID NO 258
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 258
ggagtagctt tcaattattt tggagcc                                27

<210> SEQ ID NO 259
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 259
gacttaatac agacgatggc atgggct                                27

<210> SEQ ID NO 260
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 260
gagtgcatag ctctcatgga aaaagtc                                27

<210> SEQ ID NO 261
<211> LENGTH: 25
<212> TYPE: DNA
<213> ORGANISM: Homo sapiens
<220> FEATURE:
<221> NAME/KEY: source
<222> LOCATION: 1..25
<223> OTHER INFORMATION: /mol_type="other DNA"
      /organism="Homo sapiens"

<400> SEQUENCE: 261
atgacaatga tcttagggcc acgag                                  25

<210> SEQ ID NO 262
<211> LENGTH: 23
<212> TYPE: DNA
<213> ORGANISM: Homo sapiens
<220> FEATURE:
<221> NAME/KEY: source
<222> LOCATION: 1..23
<223> OTHER INFORMATION: /mol_type="other DNA"
      /organism="Homo sapiens"

<400> SEQUENCE: 262
tagtcgaggg aggctgctct cag                                    23

<210> SEQ ID NO 263
<211> LENGTH: 21
<212> TYPE: DNA
<213> ORGANISM: Homo sapiens
<220> FEATURE:
<221> NAME/KEY: source
<222> LOCATION: 1..21
<223> OTHER INFORMATION: /mol_type="other DNA"
      /organism="Homo sapiens"

<400> SEQUENCE: 263
ctttgtccct caggcttggc c                                      21

<210> SEQ ID NO 264
<211> LENGTH: 26
<212> TYPE: DNA
<213> ORGANISM: Homo sapiens
<220> FEATURE:
<221> NAME/KEY: source
<222> LOCATION: 1..26
<223> OTHER INFORMATION: /mol_type="other DNA"
      /organism="Homo sapiens"

<400> SEQUENCE: 264
aagaggatag gctaactgac tgcctt                                 26

<210> SEQ ID NO 265
<211> LENGTH: 27
<212> TYPE: DNA

```
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 265
cagtttgcac taaatgatta caggtta                                           27

<210> SEQ ID NO 266
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 266
ataaacacta acatgtaaca ttgctagag                                         29

<210> SEQ ID NO 267
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 267
acagtctcca gagtatatta gcttagttc                                         29

<210> SEQ ID NO 268
<211> LENGTH: 29
<212> TYPE: DNA
<213> ORGANISM: Homo sapiens
<220> FEATURE:
<221> NAME/KEY: source
<222> LOCATION: 1..29
<223> OTHER INFORMATION: /mol_type="other DNA"
      /organism="Homo sapiens"

<400> SEQUENCE: 268
cattcatgaa cttagttggc aattaaatt                                         29

<210> SEQ ID NO 269
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /organism="Homo sapiens"

<400> SEQUENCE: 269
cgagctcaat tttcttgtcc ctgcttt                                           27

<210> SEQ ID NO 270
<211> LENGTH: 25
<212> TYPE: DNA
<213> ORGANISM: Homo sapiens
<220> FEATURE:
<221> NAME/KEY: source
<222> LOCATION: 1..25
```

<223> OTHER INFORMATION: /mol_type="other DNA"
      /organism="Homo sapiens"

<400> SEQUENCE: 270
acttactgtt gtgtgcagtc caagc                                        25

USE OF CFDNA FRAGMENTS AS BIOMARKERS IN PATIENTS AFTER ORGAN TRANSPLANTATION

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 64,852 Bytes ASCII (Text) file named "SEQUENCE_LISTING.TXT," created on 7 Jul. 2020.

The present invention provides methods relating to detecting donor cell-free DNA in the circulation of an organ transplant recipient for the early identification of transplant rejection.

BACKGROUND OF THE INVENTION

Every year 100,000 patients undergo organ transplantation all over the world as the only definitive treatment for end-stage organ failure.

Independently on the organ transplanted, graft rejection is a major open problem for these patients, occurring when the graft is recognized as foreign, attacked and rejected by the recipient's immune system, causing cellular damage and graft failure.

Postoperative care consists of a painful surveillance that lasts their lifetime, with frequent organ biopsies, necessary to guarantee a survival that is currently expected at 15 years.

Currently, the main monitoring methods for organ rejection upon transplantation are two:

a) tissue biopsy, that is an invasive procedure by which tissue cells are taken directly from the transplanted organ. This procedure carries several critical aspects: risk for patients, uncomfortable to be performed by doctors, expensive, feasible with sedation or anesthesia in an hospital setting, samples could be taken on unaffected graft tissue because rejection process is often focal and the number of samples taken per procedure is limited (from 5 to 8), with at least one non informative sample because it is possible to take a sample that is not included in the rejected area (useless).

b) biomarkers, whose efficiency varies for different organs and are dependent from patient features. For example approximately 50% of the function of the transplanted kidney can be lost before measurable increase of serum creatinine (kidney biomarker), depending on sex, muscle mass, or ethnicity. Conventional tests for liver function do not specifically assess acute cellular rejection (ACR).

A particular case is the example of the heart wherein approximately 7,000 of transplant/year are heart transplants (WHO Global Observatory on Donation and Transplantation).

The endomyocardial biopsy (EMB) remains the gold standard for acute rejection surveillance after Htx, but this technique entails many negative and critical features. Therefore, in solid organ transplantation, therapeutic interventions may be delayed by late diagnosis. Allogenic rejection is diagnosed and graded by histology study of the allograft biopsy (1). Acute cardiac allograft rejection remains common during the first year post-transplantation, with an incidence of over 40%, and represents a leading cause of mortality during this period, responsible for approximately 12% of fatalities (1). Moreover, an episode of rejection occurring during the first year, even when apparently successfully treated, confers higher two-year and four-year mortalities in those surviving beyond the first year, and generates independent risk factors for allograft vasculopathy (1).

The mechanisms of acute rejection in pediatric Htx recipients are similar to those occurring in adults. While infants and young children have lower acute rejection rates, adolescents have the highest acute rejection rates, with many episodes≥Grade 2R (classification ISHTL 2010, moderate acute cellular rejection) asymptomatic and detected only by surveillance EMB (2).

The EMB is an invasive technique and suffers from inter-observer variability, high cost, potential complications, and significant patient discomfort (3). Histological analysis of right ventricular myocardial tissue obtained with EMB remains the 'gold standard' technique for acute rejection surveillance; during the first postoperative year patients undergo frequent biopsies. There is no consensus on the optimal frequency of surveillance with EMB, and EMB schedules vary between Htx centers. The frequency of EMB is highest in the first 3 postoperative months with a decreasing frequency thereafter. The first year after Htx the patient undergoes about 20 EMBs. This schedule is based on the observation that the risk of allograft rejection is highest in the first 6 months and decreases sharply after 12 months. The usefulness of surveillance EMB in all patients later than 1 year after transplant is subject of debate. If the patient manifests a clinical picture consistent with allograft rejection, then it is appropriate to perform EMB, as the results may dictate changes in therapy (4). Conflicting data exist on the diagnostic yield and need for surveillance EMB in pediatric recipients. In single centers the rates of acute rejection on surveillance EMB ranges from 0.3% to 1.4% in the first year post-transplant and from 0% to 10% thereafter. Due to very low rates of rejection on surveillance EMB beyond 5 years, there is increasing consensus that EMB beyond 5 years have little usefulness in asymptomatic patients. Given the increased risk of complications in pediatric recipients, many center minimize the number of surveillance EMB in very small children and avoid them altogether in infants, while at a few pediatric center no routine surveillance EMB are performed in pre-adolescents. Furthermore, due to sampling error related to the patchy nature of acute rejection, variability in the interpretation of histological findings and non-routine screening for antibody-mediated rejection, 'biopsy negative' acute rejection (hemodynamic features suggestive of significant acute reject but apparently normal EMB) is reported to occur in up to 20% of patients. Substantial inter-observer variability exists in the grading of heart biopsies, and acute rejection may be missed when taking small samples of myocardial tissue, owing to the inhomogeneous distribution of inflammatory infiltrates and graft damage.

Furthermore, EMB is invasive, with an associated complication rate of approximately 0.5% (including myocardial perforation, pericardial tamponade, arrhythmia, access-site complications and significant tricuspid regurgitation) (5), it is expensive and it is disliked by patients, factors that prevent more frequent procedures and, thus, limit optimal titration of immunosuppressive therapy.

In children, deep sedation or general anesthesia is generally required to achieve safe vascular access and to perform the EMB. The procedure is particularly challenging in very small infants. Overall risk of serious complications with EMB in children is 0.6% (6).

In synthesis, the gold standard procedure has the advantage that it is possible to make the diagnosis of both acute rejection and infections.

However, said procedure is very invasive with an associated risk for the patient, has an inter-observer variability, needs hospitalization and a high specialized staff and depends on patient's health status.

Due to the above features, the gold standard (EMB) does not reach efficient screening and transplantation surveillance: not suitable for kids and for patients with critical physical condition, increase of the hospital saturation problem, procedure complex and time-consuming, and it involves several risks for the patient.

The ability to rapidly and reliably measure graft integrity is required to effectively adjust therapy in individual patients (i.e. to provide personalized immunosuppression) and thereby improve long-term graft survival. The fact that organ transplants are also genome transplants opens up the possibility of monitoring for allograft injury and integrity by quantification of graft-derived circulating cell-free DNA (cfDNA). In 2014 De Vlaminick et al. (7) conducted a prospective cohort study (65 patients, 565 samples) aimed at stating the potential effectiveness of cfDNA as biomarker in Htx. They used Next Generation Sequencing (NGS) technique, sequencing the whole genome, with a considerable slowdown of process time and subsequent bioinformatic analysis.

In said method the genome of the transplant donors and recipients were characterized using SNPs genotyping, on average 53,423 SNP markers, and the SNP positions with single-base alleles that were distinct between the donor and recipient and homozygous within each individual, allowed discrimination of donor- and recipient-derived sequences.

They concluded that the method was very specific (93%) but costs due to the high number of the SNPs markers used and implementation difficulties were concrete obstacles to translate these findings in clinical practice.

Snyder et al in 2011 (8) discloses a report wherein the cfDNA circulating in the blood of heart transplant recipients has been analyzed and wherein the increased levels of cfDNA from the donor genome has been observed in patients after solid organ transplant rejection, using a shot gun sequencing to measure SNP differences between individuals to quantify the donor DNA signal. The authors reported the presence of donor cfDNA at baseline (heart transplant day 0) between 0 and 1% and that the quantity of the donor cfDNA increases with rejection to at least 3-6% in heart transplantation.

The method disclosed in the document is based on the sequencing of the donor and recipient DNA and on the analysis of the informative SNP, without a selection of specific list of SNPs that can be used in a method of monitoring the status of a transplanted organ in a subject and applicable to all the samples tested.

Ollerich et al. (9) found no elevation of cfDNA in 5 patients with either intrahepatic or drug-induced cholestasis, or after liver transplant cholangiopathy who had no clinical signs of rejection. This was in contrast to conventional markers like AST and [gamma]-GT, which were highly elevated in these non-rejection conditions.

Sigdel et al in 2013 (10) used a ChrY-based sequencing method using urine from kidney transplant recipients. The method was not suitable for routine use because of the need to have specific gender (male to female) donor/recipient pairs.

Beck et al. in 2013 (11) and in WO2014/194113 used a droplet digital PCR (ddPCR) method as candidate technique for the determination of cfDNA percentages and donor/recipient discrimination. In particular, the digital droplet PCR allows for a rapid quantification of donor cfDNA in the circulation of transplant recipients as a potential universal biomarker of graft injury, by selecting no fewer than 30-35 known SNPs for high minor allelic frequencies. The accuracy of ddPCR was very promising, but the costs and the preparation time are very limiting.

Furthermore, it has been observed that said method it has the limit to be dependent on the technology of the digital droplet PCR, and it is difficult to be reproduced if the data of different laboratories are compared. Finally, the method is applicable in case of presence of a baseline with which to compare subsequent detections and to calculate a trend of variation in the ratio of donor/recipient cfDNA.

Groskovic et al in 2016 (12) and WO2015/138997 developed an assay that indirectly quantifies the fraction of cfDNA in both unrelated and related donor-recipient pairs, with a test time of 3 days, using NGS and a panel of a maximum of 266 different SNPs.

Said documents disclose a method of monitoring the status of an allograft in a transplant recipient and of adjusting immunosuppressive therapies being administered to the transplant recipients, based on the analysis of different SNPs panels for each patient tested, comprising a minimum of about 195 to a maximum of about 266 different SNPs.

In other words, it is assumed that the majority signal from the cell-free DNA sample is recipient-derived DNA and that the minority signal is donor-derived DNA, and this information can be used to calculate the levels of donor-derived DNA in the cell-free DNA sample.

Furthermore, the calculation of the percentage of the donor-derived cell-free DNA with respect to the recipient cell-free DNA in WO2015/138997, is determined on the basis of the variance in the SNP allelic distribution, by comparing said allele distribution to the expected homozygous or heterozygous distribution patterns which may be affected by sequencing errors or PCR artifacts, resulting in low precision of the final result.

Gordon et al in 2016 (13) developed an assay of 124 SNP for NGS application.

Both these last two methods applies an analysis algorithm based on the comparison between a priori probability of presence of variant allele in the SNP panel, and the a posteriori probability calculated after NGS, to inference the presence of donor DNA.

However, said methods are costly, require a long preparation, sequencing and analysis time and they need to know the genotype of the donor, which is not often accessible, or are subjected to the calculation of thresholds of significance for the inference of the presence of rejection, due to starting hypothesis on the presence or absence of donor cfDNA.

Finally, the methods are applicable only in case of presence of a baseline with which to compare subsequent detections.

There is therefore the need of a less invasive, less risky, more precise and always applicable procedure for the monitoring of patient undergoing transplantation, and of a more reliable, standardized and economic method.

X axis: % of donor cfDNA inserted in the simulated mixture (FD mixture simulated).

Y axis: % of cfDNA of the simulated donor measured with our method (FD measured).

Figure 4:
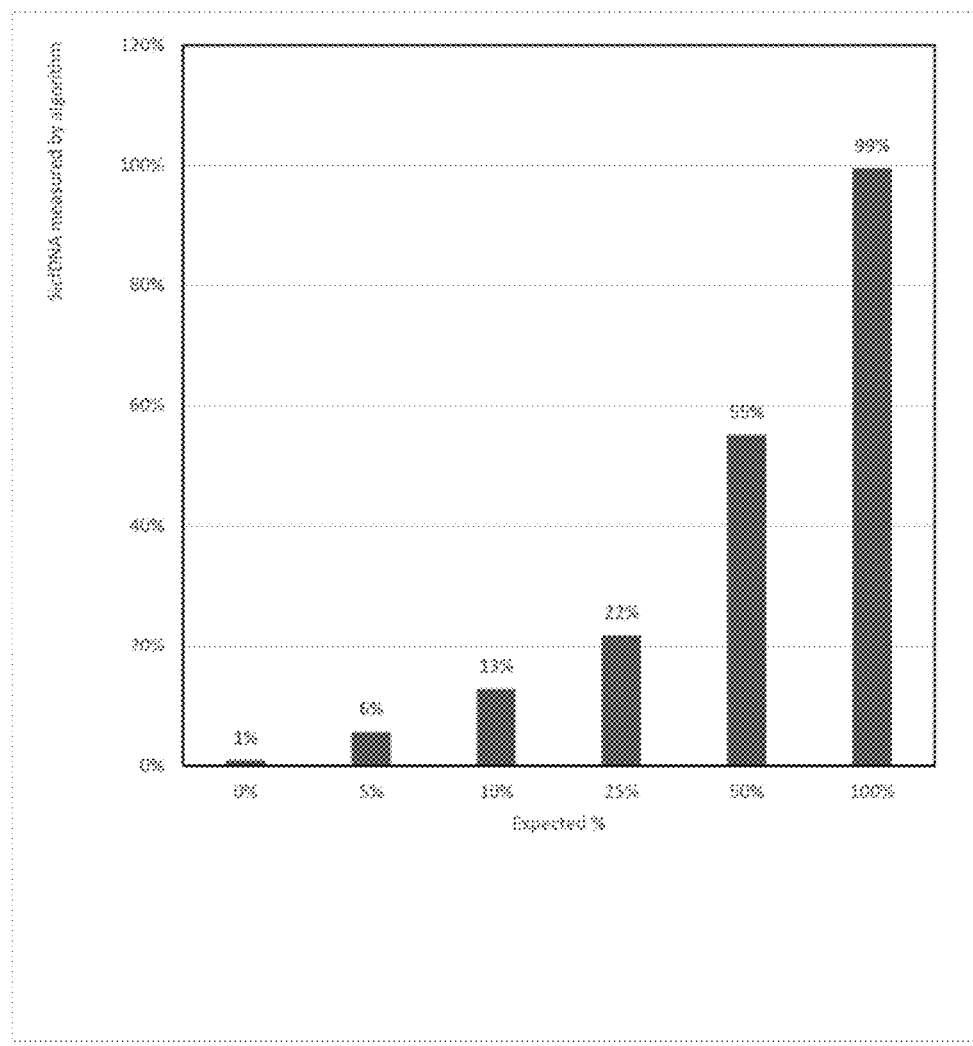

FIG. 4 shows the results of the simulation in vitro of 6 mixture of cfDNA from 2 subjects (mimicking recipient and donor), in known percentage of cfDNA of donor in recipient.

X axis: % of donor cfDNA inserted in the in vitro mixture (% expected).

Y axis: % of cfDNA of the donor measured with our method.

Figure 5:
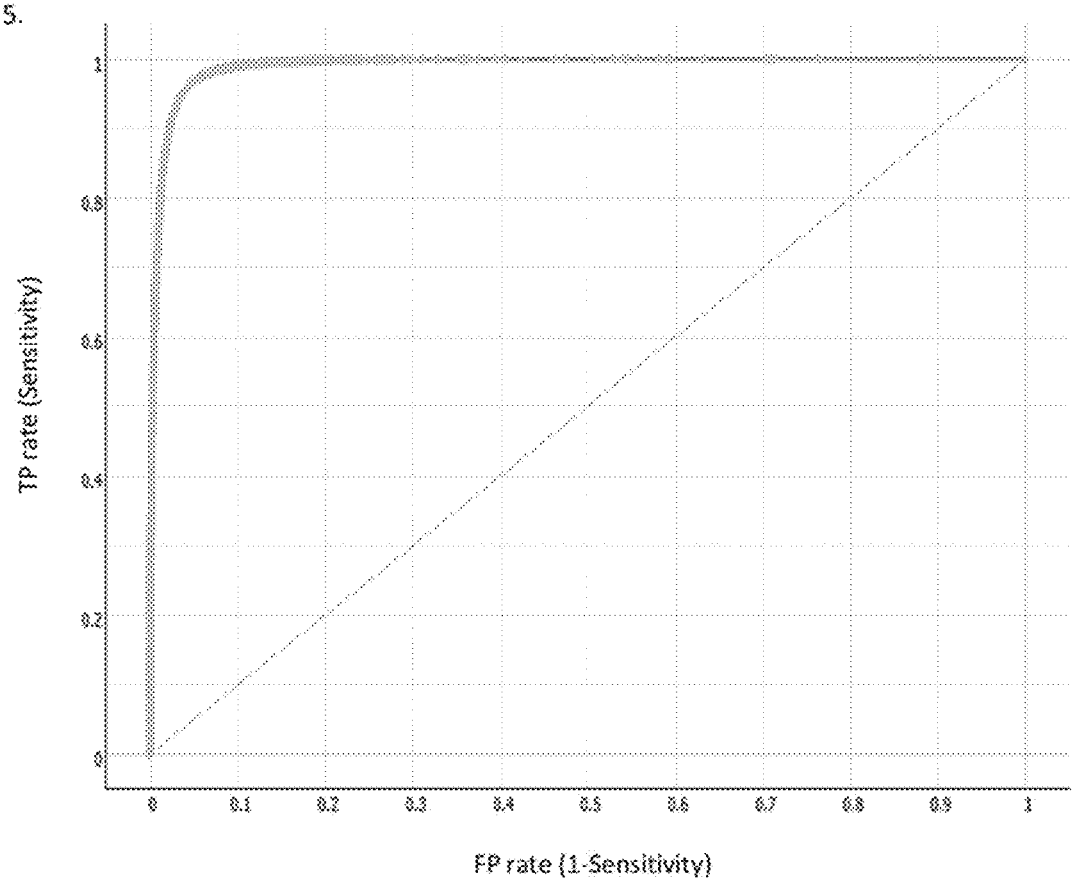

FIG. 5 shows ROC curve derived from ROC analysis (Receiver Operating Characteristic) representing the accuracy evaluation of the machine learning model after training with a simulated dataset, and tested with a random cross validation test set (20-fold validation). X axis: False Positive Rate (1-Sensitivity). Y axis: True positive rate (Sensitivity).

Figure 6:
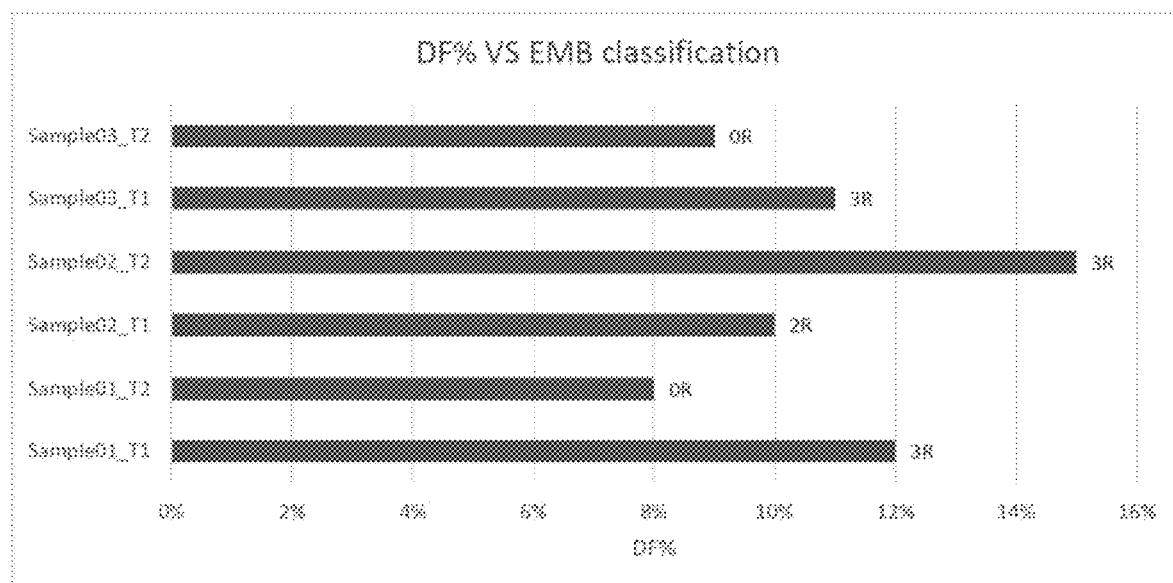

FIG. 6 shows test results on 6 real samples from 3 patients who underwent Htx. T1 was 2 weeks after Htx, T2 after 3 weeks. Labels represent EMB classification according to ISHLT guidelines. % represent Donor Fraction calculated using our test. DF %=% of donor fraction cfDNA calculated using our test.

DEFINITIONS

Unless otherwise defined, all terms of art, notations and other scientific terminology used herein are intended to have the meanings commonly understood by those persons skilled in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "circulating cell-free DNA" herein refers to the fragments of DNA/free DNA of 25 nucleotides of longer that are not associated with intact cells, released in the bloodstream after the apoptosis of cells.

A "single nucleotide polymorphism (SNP)" in the context of this invention refers to the presence of an alternative base in specific positions of DNA sequence, chosen to characterize DNA genotype of an individual with respect with another. Such a SNP is a geno-marker for donor material.

The term "variant" herein refers to the presence of an alternative DNA base in a particular position of DNA sequence, referring to universally recognized reference sequence (GRCH37).

The term "allele frequency" herein refers to the relative frequency (percentage) of an alternative base in a particular position of the DNA, referring to universally recognized reference sequence (GRCH37), calculated on the total amount of sequences in that position.

The terms "approximately" and "about" herein refers to the range of the experimental error, which may occur in a measurement.

The terms "comprising", "having", "including" and "containing" are to be construed open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as semi-closed terms, meaning that no other ingredients which materially affects the basic and novel characteristics of the invention are included (optional excipients may thus be included).

The terms "consists of", "consisting of" are to be construed as closed terms.

DESCRIPTION OF THE INVENTION

It has been surprisingly found that by sequencing a panel of 94 single nucleotide polymorphisms (SNPs) from cell-free DNA from a sample obtained by a subject who is the recipient of an organ transplant, it is possible to differentiate between donor-derived cell-free DNA and recipient-derived cell-free DNA, and therefore to correlate the graft damage to the quantity of graft cell-free DNA released from damaged cells in patients.

In particular, it has been demonstrated that the selection of a pre-determined number of SNPs, in particular of a panel of 94 SNPs reduce the possibility to obtain the false positive during the sequencing phase, that could be very high analyzing cfDNA, that is usually very fragmented.

This is based on the fact that, during acute rejection the recipient's immune system recognizes the transplanted organ as alien, it attacks the organ and causes cellular damage, thus resulting in dispersion of nuclear DNA from the donor organ cells in the recipient's bloodstream.

This DNA, called donor "circulating cell-free DNA (cfDNA)", is distinctive for the donor and it can be recognized from the one of the recipient, physiologically present in a small quantity in recipient blood stream, because of normal necrosis of cells like endothelial ones.

The greater is the amount of donor cfDNA in the recipient blood, the greater is the graft damage caused by the recipient immune system, therefore calculating the amount of said cfDNA it is possible to correlate the graft damage to the level of graft DNA released from damaged cells in patient.

In particular, our method is based on a simple biological observation related to acute and chronic rejection: the immune response to allograft that damages graft cells, which release cellular residues in the bloodstream. These cellular residues include highly fragmented but detectable cell-free DNA in plasma. This damage induces identifiable and quantifiable chimerism in the blood of the recipient. The assumption is that, during acute rejection, the increased amount of molecules derived from the donor (and therefore derived from the implanted organ) are present in the blood stream of the recipient and increases with the increase of the extent of organ damage.

Our goal is to directly interrogate the graft status, individuating and measuring the DNA fingerprint of dying allogenic cells in the cell-free DNA circulating in the recipient's plasma. If the fingerprint of DNA from the donated organ (compared with the recipient's genome) is characterized, then the presence and level of "donor cfDNA" can be monitored over time. Changes in organ status can be detected as changes in the donor cfDNA levels. The rationale for this approach arises from the observation that both acute and chronic rejection processes are associated with apoptosis of organ-specific cell types within the allograft. An increase of graft DNA from 1% to 5% during rejection episodes has been reported in the circulation of stable heart transplant recipients, while an increase of graft DNA>5% is indicative of a beginning of rejection.

From the experiments made in our laboratory we observed that sequencing an high number of SNP, such as different panels from 138 to 155 SNPs (see Table n. 1), we had an high number of false positive and we obtained a method with a lower precision and very laborious.

Based on said results we identified a method with a panel of 94 SNPs previously identified that was able to differentiate between two unrelated individuals.

In particular, the system of our method is composed by a panel of specific genetic markers, named SNPs (single nucleotide polymorphisms), and by an analysis algorithm specifically designed to discriminate two individuals, the donor and the recipient, using a specific identified panel of 94 SNPs and quantifying the cfDNA fraction from the donor.

For each experiment, we process a pair of genomic DNA, from the donor and from the recipient, and the total cfDNA from the recipient (individual 1) blood samples. The aim is to identify the presence of the donor (individual 2) cfDNA, using the genomic the DNA from recipient and from donor as reference.

In case of impossibility of process genomic DNA sample from donor, we process genomic DNA and total cfDNA, using the genomic DNA of the recipient as unique reference.

The advantages of the new method developed is that with at least one SNP of difference between the donor and the recipient it is possible to identify the presence of the cfDNA of the donor in a blood sample and to quantify it, without the need of donor genomic DNA as reference.

Furthermore, our method has a low limit of detection (1%) and therefore it is possible to identify up to 1% minimum donor cfDNA fraction in total cfDNA (recipient+donor), and a very high sensitivity (>98%) and a low incidence of false negative (≤1%). Therefore the algorithm used in the method is able to correctly identify SNPs positions in the panel and to identify variants in that positions and to calculate the percentage of the donor-derived cell free DNA with respect to the recipient cell-free DNA, using the recipient genomic DNA as reference.

One aim of the present invention is therefore a method of monitoring the status of a transplanted organ in a subject, comprising:
a) providing cell-free DNA from a biological sample obtained from a subject who is the recipient of an organ transplant from a donor;
b) sequencing a panel of 94 single nucleotide polymorphisms (SNPs) from the cell-free DNA; and
c) calculating the quantity the donor-derived cell-free DNA in said biological sample.

According to a preferred embodiment, the cell-free DNA isolated in step a) from the transplant recipient can be extracted from methods and protocols for DNA extraction well known in the art.

Said method are preferably selected from Qiagen QIAamp MinElute ccfDNA Kits, Maxwell RSC cfDNA Plasma Kit, Invitrogen MagMAX Cell-Free DNA Isolation Kit. In a preferred embodiment of the present invention the panel of 94 single nucleotide polymorphisms sequenced at point b) include the SNP listed in Table 3.

The selection of said panel of 94 SNP was made identifying the SNPs that are useful to identify uniquely one individual from another (45 SNP identified as iiSNP in forensic genetic (14)) and that have a high variability, easily to be mapped and with a fixation index of 0.06 (49 SNP, selected from alfred.med.yale.edu/, last accessed April 2017).

In a further preferred embodiment, the SNP sequencing is made with the primers listed in Table 4.

According to the present invention, the methods of sequencing DNA disclosed in step b) are selected from the next generation sequences method and instruments known in the art (i.e Illumina platforms, Ion-Torrent, MinION, GeneRead, PacBio).

Preferably, said methods of sequencing the DNA are selected from amplicon method, capture method, enrichment method, pyrosequencing, incorporation of nucleotides, semiconductor technologies, nanopore real time reading and sequencing methods without PCR.

The bioinformatics analysis used in the method of the present invention is similar to the one used to identify somatic mutations in tissue. In particular, said bioinformatics analysis compares recipient genomic DNA with cfDNA, searching for variants in cfDNA. The presence of those variants can be associated only to sequencing errors or donor DNA coming from the graft cells destruction due to rejection. The analysis excludes errors identifying real variants in specific positions (SNPs).

According to a preferred embodiment, the method of the present invention is characterized in that step c) calculate the differences in SNP positions by identifying and comparing variations in specific nucleotide positions between the donor-derived cell-free DNA and the recipient-derived cell-free DNA using the recipient genomic DNA previously characterized, as reference.

In a further preferred embodiment the step c) of the method according to the present invention is based on the calculation of cfDNA donor fraction with the formula:

$$DFi\% = (AF(SNPi) - AF(SNPi_{rec}))/(AF(SNPi_{don}) - AF(SNPi_{rec}))*100$$

for each SNPi and total DF % is calculated as: DF %=mean DFi %±SD DF where:

$AF(SNP_i)$ is the allele frequency of the SNP considered, calculated by the algorithm for the total cfDNA mixture (donor+recipient), and $AF(SNP_{idon})$ and $AF(SNP_{irec})$ is the allele frequency of the SNP considered in the donor and recipient cfDNA respectively, according to their genotype, SNPs where the transplant, material and recipient are homozygous, but with different alleles, can then be used for future determination of graft cfDNA percentage.

Preferably, said algorithm is composed by 2 parts: the first part is aimed at identifying the 94 variants (SNPs panel), the second part is aimed at identifying genotype of donor and recipient, distinguishing cfDNA reads from 2 individuals, and calculate donor fraction.

The steps used in the first part are:
Alignment of the sequence to the GRCH37 human genome using a well-known algorithm selected from BWA, BWA-MEM or Novoalign.
Pre-processing of the aligned sequence to reduce sequencing or alignment errors using dedicated open source algorithms selected from GATKv3.7 or Picard v2.7.
Variant Calling using a known open source algorithm for variant identification in a case-control analysis selected from Mutect2, VarDictJava, GATK v3.7, Varscan v2.3.9 or Freebayes v0.9.10.
Post-processing and feature extraction: during post-processing, variants obtained from each variant caller are merged into a single dataset, reporting all features in a tsv file format.

The second part of analysis is aimed at identifying genotype of donor and recipient, distinguishing cfDNA reads from 2 individuals, and calculate donor fraction.

The steps used in second part are:
Variant filtering: wherein variants are classified as PASS or FILTER to identify TP and FP on the basis of quality of sequencing and coverage. In this step the 94 SNPs are identified (as variant annotation) and considered for further analysis.

Genotype identification: in case of absence of donor DNA, the algorithm applies a supervised machine learning inference model, preferably based on the posterior Bayes probability (Naïve Bayes), to classify each new SNP independently. The machine learning can be applied using a Python based package such as Scikit-Learn, Teano, Tensor Flow or Weka, STATA, Orange or R software for data analysis.

Donor fraction calculation: the donor fraction is calculated using the formula described above for each SNP. The mean of donor fraction of all informative SNPs is calculated. In case of absence of donor genotype, a weighted mean value for each genotype is calculated.

Reporting of results: for each sample a report is create containing the SNP identified, the genotype, the presence of variants referable to donor and the amount of donor cfDNA (DF %).

Figure 1:
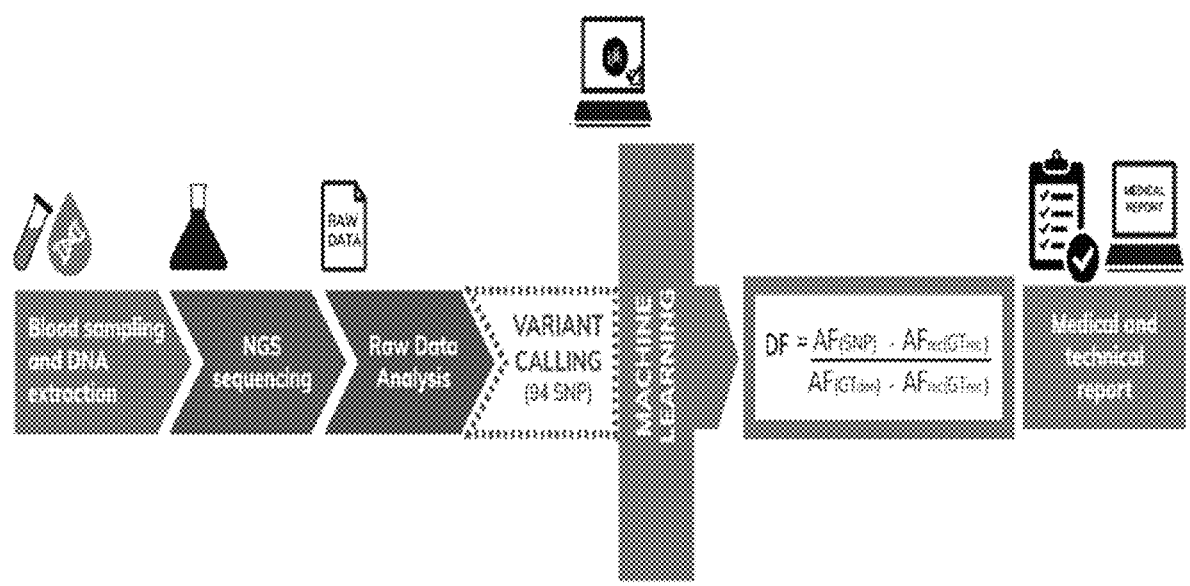
FIG. 1 shows the entire test procedure, from blood sampling to donor fraction calculation and algorithm.
Figure 2:
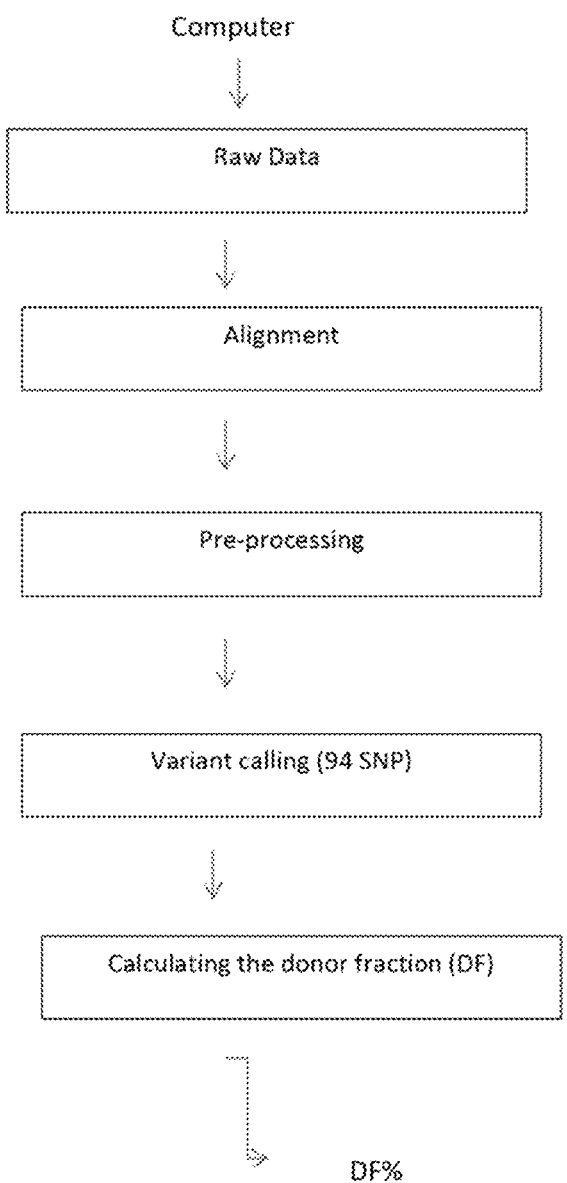
FIG. 2. Computer readable instructions: from raw data to DF %.

A scheme of the entire algorithm is represented in FIG. 2.

$AF(SNP_i)$ and $AF(SNP_{irec})$ for each SNP found in the tested sample is calculated by the algorithm on the basis of the sequence obtained by the instrument.

In case of the availability of the genomic donor DNA, also the $AF(SNP_{idon})$ is calculated by the algorithm and the unique unknown variable in the formula is DF, otherwise $AF(SNP_{idon})$ is deduced using a supervised machine learning model using as attributes quality of the sequence in that position, $AF(SNP_{irec})$ and $AF(SNP_i)$ and relative genotypes.

Preferably, said supervised machine learning model is based on the posterior Bayes probability (Naïve Bayes), to classify each new SNP independently.

In a preferred embodiment, in the method according to the present invention the transplanted organ is selected from heart, lung, kidney, liver or pancreas.

In particular, the method of the present invention is applicable to all the transplanted organs, because the presence of cfDNA is organ independent.

According to the method of the present invention, the number of SNPs sequenced will be sufficient to discriminate between recipient and donor alleles even in related individuals (excepting twins).

In a preferred embodiment the biological sample used on the claimed method is a blood sample from the recipient, and a blood or tissue sample from donor, if present.

According to the present invention, the diagnosis of the status of the transplanted organ in the subject is made evaluating the percentage and/or the quantity of the donor-derived cell-free DNA with respect to the recipient cell-free DNA, using the recipient genomic DNA as reference.

Preferably, a change in the percentage of the donor-derived cell-free DNA during a period of time is indicative of the status of the transplanted organ.

According to the method of the present invention, an increase in the levels of the donor-derived cell-free DNA over the time interval is indicative of transplant rejection, a need for adjusting immunosuppressive therapy, and/or a need for further investigation of the transplanted organ status.

Preferably, an increase in level of cfDNA comprised between 5 and 15% is indicative of probably presence of rejection, more preferably an increase of 10 to 25% is indicative of clinically significant rejection.

In a further embodiment, a decrease in the levels of the donor-derived cell-free DNA over the time interval is indicative of transplant tolerance, a need for adjusting immunosuppressive therapy, and/or a need for further investigation of the transplanted organ status; while a value under 5% or no change in the levels of the donor-derived cell-free DNA over the time interval is indicative of stable transplant rejection status and/or opportunity for adjusting immunosuppressive therapy.

Preferably, a decrease in level of cfDNA comprised between 10 and 25% from the positive evaluation is indicative of efficacy of immunosuppressive therapy. More preferably, said decrease is comprised between 15 and 20%.

According to the present invention, the biological samples may be taken from a transplant recipient over a period of time (i.e. over a time interval). The time at which samples are taken from the transplant recipient following the transplant event may vary. Samples may be taken from a transplant recipient at various times and over various periods of time for use in determining the status of the allograft according to the methods of the present disclosure. For example, samples may be taken from the transplant recipient within days and weeks after, about three months after, about six months after, about nine months after, or less than one year after the transplant event. Samples may be taken from the transplant recipient at various times before the one year anniversary of the transplant event, at the one year anniversary of the transplant event, or at various times after the one year anniversary of the transplant event. For example, at the one year anniversary after a transplant, samples may begin to be taken from the transplant recipient at month 12 (i.e. the one year anniversary of the transplant event) and continue to be taken for periods of time after this.

In some embodiments, a transplant recipient has biological samples taken for one to three consecutive months, starting at the one year anniversary of the transplant event (i.e. 12 months after the transplant event), providing a total of 4-6 samples for analysis taken over a three month time period, with samples being collected about every two weeks. In some embodiments, a transplant recipient has samples of bodily fluid taken once a week for one to three consecutive months, starting at the one year anniversary of the transplant event (i.e. 12 months after the transplant event), providing a total of twelve samples for analysis taken over a three month time period. The total duration of obtaining samples from a transplant recipient, as well as the frequency of obtaining such samples, may vary and will depend on a variety of factors, such as clinical progress. For example, a transplant recipient may have samples obtained for analysis of cell-free DNA for the duration of their lifetime.

Appropriate timing and frequency of sampling will be able to be determined by one of skill in the art for a given transplant recipient.

The methods of the present disclosure may be used to predict the risk of future transplant rejection such as, for example, the risk of rejection within the following 3-6 months after analysis of samples from the transplant recipient.

The methods of the present disclosure may also be used provide an assessment of the immune status of the transplant recipient, which may be used to guide decisions regarding immunosuppressive therapy in the transplant recipient. The methods of the present disclosure may also be used to guide decisions related to adjustment of immunosuppressive therapies being administered to the transplant recipient, with regard to the presence or level of rejection identified.

Additional benefits and/or uses of the methods of the present disclosure will be readily apparent to one of skill in the art.

In a further embodiment, the invention provides a method of monitoring the status of a transplant in a transplant recipient to evaluate immunosuppressive therapy where the method comprises quantifying the amount of the donor derived cell-free DNA in a sample from the transplant recipient at desired time points and adjusting the immunosuppressive therapy, e.g., adjusting the amount of immunosuppressive drug.

Thus, the lowest dose of an immunosuppressive drug can be identified for that individual patient.

In a further aspect, the invention provides a method of monitoring the status of a transplant in a transplant recipient to evaluate reperfusion injury to the transplant, in such embodiments, the amounts of graft cfDNA are determined over a time course, for example, a time course of days or weeks up to a month following transplant.

Preferably, cfDNA is monitored over the first 7 days after engraftment.

In a further embodiment, the method comprises determining the level of graft cfDNA over a course of seven days, or up to 30 days following transplant.

In a further aspect, the invention provides a method of monitoring the status of the transplanted graft with respect to Antibody-Mediated Rejection (AMR) in a transplant recipient to evaluate status of the graft. In such embodiments, the amounts of graft cfDNA are determined after 2 years from the transplanted. The presence of AMR will determine changes in the immunosuppressive therapy strategy.

A further embodiment of the present invention relates to a computer program product comprising a computer-usable medium having computer-readable program codes or instructions embodied thereon for enabling a processor to carry out the analysis and correlating functions as described above.

A further embodiment of the present invention is a computer medium comprising instructions which, when executed by a computer, cause the computer to carry the following steps:

(i) receiving raw data from SNP sequences obtained from the method of claim 1;

(ii) aligning said sequencing data with the referring genome;

(iii) preprocessing and preparing raw data for variant calling;

(iv) identifying SNP variants and calculating the genotype of the recipient for these SNP, identifiable as not mutated (0/0), mutated heterozygous (0/1) or mutated homozygous (1/1), through a germline variant calling process;

(v) calculating the genotype of the cfDNA mixture and comparing it with the calculated recipient one through a somatic variant calling process;

(vi) calculating the donor fraction according to the following formula:

$$DFi\% = (AF(SNP_i) - AF(SNP_{irec}))/(AF(SNP_{idon}) - AF(SNP_{irec})) \times 100$$

$$DF\% = \text{mean } DF_{i\%} \pm SD\ DF_i$$

Preferably, said method is a computer readable list of instructions according to FIG. 2 recorded to cause a computer to perform the steps reported above.

EXAMPLES

Example 1

SNP Panel Design

Using our bioinformatics background and new knowledge developed in forensic genomics on individual discrimination (15), we designed a Single Nucleotide Polymorphisms (SNPs) panel, containing so-called individual identification SNPs. The goal of the SNP panel design solution was to be able to discriminate the presence of fragments of DNA of a different person from the one in which the blood sampling was done.

Before identifying the more appropriate number of SNP that lead to the reliable, precise and economic method according to the present invention, we started using a different number of SNP, variable from 138 to 155 SNPs, having as principal characteristic a high variability and a difference homozygous/homozygous between donor and recipient.

As reported in Table n. 1 this lead to a method with very low precision and accuracy (from 40-50%) and a high number of false positive.

TABLE 1

Results of simulation of different concentrations of cfDNA of individual 1 and 2 and a panel of SNP from 138-155: statistics.

| cfDNA Concentration | NUM SNPs | PRECISION | ACCURACY |
|---|---|---|---|
| 0.50% | 135 | 45.22% | 40.51% |
| 0.80% | 143 | 48.57% | 46.12% |
| 1% | 150 | 50.64% | 50.11% |
| 5% | 150 | 50.64% | 50.11% |
| 10% | 151 | 50.84% | 50.51% |
| 50% | 151 | 50.84% | 50.51% | cfDNA Concentration: concentration of an individual's cfDNA, in the total cfDNA of the two individuals.
NUM (SNPs): number of SNP identified;
PRECISION: or positive predictive value, proportion of positive call, really positive
ACCURACY: proportion of true results among the total number of cases examined.

As it can be observed form Table 1, the method based on a panel of 138-155 SNPs was not sufficient to identify clearly between the 2 individuals, due to the high number of false positive detected. Therefore, a lower number of more precise SNP should be used to increase performance of the method.

Based on the non-optimal results obtained with a panel of a higher number of SNPs, we made the same experiments with an identified panel of 94 SNPs previously identified as suitable for differentiating between any two unrelated individuals. We choose SNPs with a high frequency of mutation in general population (independently of gender or ethnicity), to be sure to find a minimal percentage of SNPs of the panel, different in every combination of two individuals. The rationale was to discriminate cfDNA of the donor through identification of SNPs different from the recipient.

The obtained panel is composed by 94 SNPs. This combination of SNPs has an extremely low probability for two unrelated individuals having identical genotypes. All SNPs have an average heterozygosity>0.4 and/or a Fst>0.06. Fixation index (Fst) is a measure of population differentiation due to genetic structure, the values range from 0 to 1. A zero value implies complete panmixia (random mating); that is, that the two populations are interbreeding freely; a value of one implies that all genetic variation is explained by the population structure, and that the two populations do not share any genetic diversity. The chosen value makes this a universally applicable panel irrespective of ethnicity or ancestry (Table 1). The frequencies of SNPs were verified in 1000Genomes (www.internationalqenome.org/1000-genomes-browsers/, last accessed 19 Jan. 2019).

TABLE 2

Results of simulation of different concentrations of cfDNA form individual 1 and 2 and a panel of 94 SNPs: statistics.

| cfDNA Concentration | NUM SNPs | Accuracy | Precision |
|---|---|---|---|
| 0.50% | 94 | 79.63% | 79.63% |
| 0.80% | 94 | 90.13% | 90.13% |
| 1% | 94 | 97.93% | 97.93% |
| 5% | 94 | 98.71% | 98.71% |
| 10% | 94 | 98.71% | 98.71% |
| 50% | 94 | 98.71% | 98.71% |

NUM SNPs: number of SNP identified;
PRECISION: or positive predictive value, proportion of positive call, really positive
ACCURACY: proportion of true results among the total number of cases examined.

The results obtained with this new panel were very promising in terms of accuracy and precision (95-100%), with a high accuracy and precision with respect to the panel of 138-155 SNPs reported in Table 1.

TABLE 3

List of 94 SNPs panel. (www.ncbi.nlm.nih.gov/projects/SNP/, last accessed 19/1st/2019), Fst, heterozygosity and reference populations for calculation from ALFRED (alfred.med.yale.edu, last accessed 19/1st/2019).

| dnSNP rs# | Fst | Avg Het | # Samples |
|---|---|---|---|
| rs159606 | 0.045 | 0.434 | 108 |
| rs214955 | 0.059 | 0.47 | 100 |
| rs221956 | 0.035 | 0.454 | 132 |
| rs251934 | 0.088 | 0.355 | 127 |
| rs279844 | 0.037 | 0.48 | 66 |
| rs321198 | 0.053 | 0.461 | 77 |
| rs338882 | 0.075 | 0.459 | 99 |
| rs354439 | 0.166 | 0.416 | 109 |
| rs430046 | 0.045 | 0.44 | 106 |
| rs445251 | 0.051 | 0.466 | 76 |
| rs560681 | 0.032 | 0.434 | 68 |
| rs576261 | 0.045 | 0.47 | 107 |
| rs717302 | 0.235 | 0.376 | 126 |
| rs719366 | 0.067 | 0.377 | 94 |
| rs722098 | 0.219 | 0.39 | 142 |
| rs722290 | 0.044 | 0.477 | 88 |
| rs727811 | 0.144 | 0.428 | 145 |
| rs729172 | 0.113 | 0.37 | 96 |
| rs733164 | 0.213 | 0.383 | 126 |
| rs735155 | 0.145 | 0.426 | 94 |
| rs737681 | 0.149 | 0.358 | 128 |
| rs740598 | 0.035 | 0.458 | 67 |
| rs740910 | 0.223 | 0.294 | 94 |
| rs763869 | 0.095 | 0.422 | 97 |
| rs826472 | 0.104 | 0.326 | 57 |
| rs873196 | 0.067 | 0.347 | 126 |
| rs876724 | 0.086 | 0.351 | 95 |
| rs891700 | 0.044 | 0.475 | 129 |
| rs901398 | 0.051 | 0.436 | 95 |
| rs907100 | 0.143 | 0.428 | 95 |
| rs914165 | 0.15 | 0.423 | 94 |
| rs13218440 | 0.043 | 0.459 | 99 |
| rs917118 | 0.14 | 0.417 | 145 |
| rs938283 | 0.062 | 0.239 | 77 |
| rs964681 | 0.059 | 0.424 | 94 |
| rs987640 | 0.058 | 0.471 | 66 |
| rs993934 | 0.057 | 0.448 | 107 |
| rs1005533 | 0.12 | 0.421 | 126 |
| rs1015250 | 0.21 | 0.388 | 94 |
| rs1024116 | 0.131 | 0.41 | 109 |
| rs1028528 | 0.253 | 0.351 | 50 |
| rs1031825 | 0.079 | 0.435 | 94 |

TABLE 3-continued

List of 94 SNPs panel. (www.ncbi.nlm.nih.gov/projects/SNP/, last accessed 19/1st/2019), Fst, heterozygosity and reference populations for calculation from ALFRED (alfred.med.yale.edu, last accessed 19/1st/2019).

| dnSNP rs# | Fst | Avg Het | # Samples |
|---|---|---|---|
| rs1058083 | 0.037 | 0.456 | 108 |
| rs1109037 | 0.048 | 0.471 | 68 |
| rs1294331 | 0.062 | 0.445 | 123 |
| rs1335873 | 0.243 | 0.369 | 143 |
| rs1336071 | 0.043 | 0.472 | 67 |
| rs1355366 | 0.185 | 0.358 | 95 |
| rs1357617 | 0.094 | 0.298 | 95 |
| rs1360288 | 0.09 | 0.361 | 94 |
| rs1382387 | 0.121 | 0.399 | 94 |
| rs1413212 | 0.058 | 0.431 | 105 |
| rs1454361 | 0.086 | 0.456 | 94 |
| rs1463729 | 0.093 | 0.447 | 120 |
| rs1490413 | 0.066 | 0.465 | 96 |
| rs1493232 | 0.075 | 0.457 | 94 |
| rs1498553 | 0.033 | 0.483 | 67 |
| rs1523537 | 0.06 | 0.465 | 98 |
| rs1528460 | 0.226 | 0.386 | 126 |
| rs1736442 | 0.056 | 0.438 | 100 |
| rs1821380 | 0.034 | 0.467 | 66 |
| rs1886510 | 0.162 | 0.345 | 135 |
| rs1979255 | 0.093 | 0.448 | 95 |
| rs2040411 | 0.169 | 0.41 | 148 |
| rs2046361 | 0.083 | 0.455 | 105 |
| rs2056277 | 0.07 | 0.242 | 127 |
| rs2076848 | 0.17 | 0.381 | 94 |
| rs2107612 | 0.076 | 0.363 | 93 |
| rs2111980 | 0.073 | 0.456 | 126 |
| rs2269355 | 0.052 | 0.473 | 48 |
| rs2342747 | 0.044 | 0.424 | 106 |
| rs2399332 | 0.052 | 0.432 | 107 |
| rs2830795 | 0.081 | 0.355 | 57 |
| rs2831700 | 0.077 | 0.451 | 134 |
| rs2920816 | 0.046 | 0.443 | 106 |
| rs3780962 | 0.044 | 0.478 | 99 |
| rs4364205 | 0.054 | 0.441 | 108 |
| rs4530059 | 0.053 | 0.407 | 107 |
| rs4606077 | 0.05 | 0.423 | 106 |
| rs6444724 | 0.045 | 0.47 | 100 |
| rs6811238 | 0.032 | 0.483 | 67 |
| rs6955448 | 0.037 | 0.413 | 108 |
| rs7041158 | 0.053 | 0.437 | 106 |
| rs8037429 | 0.056 | 0.469 | 93 |
| rs8078417 | 0.037 | 0.408 | 65 |
| rs9905977 | 0.049 | 0.427 | 106 |
| rs9951171 | 0.034 | 0.478 | 66 |
| rs10092491 | 0.047 | 0.451 | 99 |
| rs10488710 | 0.019 | 0.449 | 67 |
| rs10495407 | 0.106 | 0.345 | 97 |
| rs10773760 | 0.044 | 0.445 | 106 |
| rs10776839 | 0.062 | 0.46 | 110 |
| rs12997453 | 0.054 | 0.434 | 68 |
| rs13182883 | 0.039 | 0.466 | 67 |

Each of the SNPs in the panel reported in Table 3 can be present in the donor and recipient as not mutated (0/0 or reference homozygous), mutated homozygous (1/1 or alternative homozygous), or heterozygous 0/1 or 1/0.

In order to discriminate uniquely the 2 unrelated individuals, only combinations specifically different from recipient and donor such as 0/0-0/1 or 0/0-1/1 are useful for the analysis.

Analysis Algorithm

An ad hoc analysis pipeline of NGS data was developed using software packages developed in Unix Bash, including several bioinformatic tools and Python scripts. The pipeline is based on the contemporary calculation of genotype (GT) of samples analyzed, using a germline and a somatic pipeline for NGS identification of variants.

The germline pipeline is focused on identification of genotype in genomic DNA of individual 1.

Pipeline for parallelized germline genotype identification and somatic identification of differences is reported below.

Alignment: FASTQ files coming out from Illumina sequencer are aligned using BWA-MEM v 0.7.15 tool.

Pre-processing: SAM file obtained are then converted in BAM files and sorted using picard v2.7. Read Group are added. Target Amplicon analysis includes a data-cleaning step to reduce False Positive and False Negative using Base Quality Score Recalibration using GATK v3.7 and BAM file are indexed using picard v2.7.1

Variant Calling: this step involves the usage of three variant callers to increase sensitivity. Somatic pipeline performs a case-control analysis using Mutect2, VarDictJava e VarScan v2.3.9, where case is cfDNA and control is the genomic DNA. All variant callers are used without filters. The genomics DNA genotype is also called by three variant callers (GATK v3.7, Varscan v2.3.9 and Freebayes v0.9.10) for germline analysis. The genomic DNA gives the genotype information about individual 1, to be used in reporting phase. All variant callers are used with default parameters.

Post-processing and feature extraction: during post-processing, variants obtained from each variant caller are merged into a single dataset, reporting all features in a tsv file format.

Variant filtering: variants are classified as PASS or FILTER to identify TP and FP on the basis of quality of sequencing and coverage. The 94 SNPs are identified (variant annotation) and considered for further analysis.

Genotype identification: in case of absence of donor DNA, the algorithm applies a supervised machine learning inference model based on the posterior Bayes probability (Naïve Bayes), to classify each new SNP independently. Weka 3.8.1 was used for calculation.

Donor fraction calculation: donor fraction is calculated using the formula described above for each SNP. The mean of donor fraction of all informative SNPs is calculated. In case of absence of donor genotype, a weighted mean value for each genotype is calculated.

Reporting of results: For each sample a report is create containing SNP identified, genotype, presence of variants referable to donor and amount of donor cfDNA (DF %).

Materials and Methods cfDNA Extraction

Whole blood (6 ml) was collected in blood collection tubes (BD tubes with EDTA). Blood was centrifuged at either 4,000 rpm (larger volumes) or 13,000 rpm (smaller volumes) at 4° C. for 15 min, the plasma removed, and centrifuged again at 13,000 rpm at 4° C. for 15 min and the supernatant frozen at −80° C. until used.

In 10 blood samples (3 ml) from 10 unrelated voluntary donors, plasma was separated and cfDNA was purified using both a semi-automated or completely automated method: Qiagen (QIAamp Circulating Nucleic Acid Kit) and Promega (Maxwell® RSC ccfDNA Plasma Kit), according to both protocols, respectively. cfDNA concentration was measured using the Qubit dsDNA HS Assay kit (Invitrogen, Life Technologies, CA, USA) on a Qubit 2.0 Fluorometer (Invitrogen, Life Technologies, CA, USA) according to manufacturer's instructions.

Libraries Preparation and Sequencing

The cfDNA assay is based on targeted amplification of DNA regions harboring 94 SNPs. cfDNA extracted from 1 mL plasma or reference materials was pre-amplified in a single multiplex reaction with 270 primer (see Table 2) pairs for 15 cycles. Preparation protocol used were Illumina Truseq Custom Amplicon for target sequencing. Index sequences and Illumina sequencing adapters were added to each sample DNA by PCR, and the sample was qualified and quantified by Qubit 2.0 Fluorometer (Invitrogen, Life Technologies, CA, USA) and an Agilent Technologies 2100 Bioanalyzer (Agilent, Santa Clara, CA), according to preparation protocols. Up to 24 amplified samples were pooled in equimolar amounts, purified using Agencourt AMPure XP beads (Beckman Coulter, Brea, CA), and sequenced on an Illumina MiSeq instrument.

Table 4 reports SNP primers of target amplicons used for experiments. Some SNPs are covered by more than one target to ensure the complete coverage of the panel.

TABLE 4

Target (primers) used in experimental setting.

| TARGET REGION NAME | CHROMO-SOME | 5' SEQUENCE (FORWARD)* | 3' SEQUENCE (REVERSE)** |
|---|---|---|---|
| rs1005533 | chr20 | TCAGACCCTAGTCCCAGCTGGGTGAG (SEQ ID NO: 1) | TTGGGGGCATCTGAAACACTCACACAC (SEQ ID NO: 2) |
| rs1005533 | chr20 | TTCCCTGGTCTTGCCCCTGCACT (SEQ ID NO: 3) | CAATGCTCACAGAGATCTCCCAGATCA (SEQ ID NO: 4) |
| rs10092491 | chr8 | GAATCCACAGCTGCAGAAAACCAAATG (SEQ ID NO: 5) | TCTATCACAGAATTATTTATATATGGCCCA (SEQ ID NO: 6) |
| rs1015250 | chr9 | CGACATGGGAAATGTCAGATCATAAGACAT (SEQ ID NO: 7) | CTTTGGATTCTAAAGTGGATCTAATAACAG (SEQ ID NO: 8) |
| rs1015250 | chr9 | AGCATTTAAACAGCTATGAATCCACCT (SEQ ID NO: 9) | TTTCAACATGCCCTTAGGGAATTCATG (SEQ ID NO: 10) |
| rs1024116 | chr18 | CAATAACGTCCAGGGAGTGAAAAATCC (SEQ ID NO: 11) | TACATGTTCCACTTCCCATGTGCTC (SEQ ID NO: 12) |
| rs1028528 | chr22 | TCACCAGCCCCAGCAAGGGCATGGGA (SEQ ID NO: 13) | AAGACCACAGGTCAGGGAGGCAT (SEQ ID NO: 14) |

TABLE 4-continued

Target (primers) used in experimental setting.

| TARGET REGION NAME | CHROMO-SOME | 5' SEQUENCE (FORWARD)* | 3' SEQUENCE (REVERSE)** |
|---|---|---|---|
| rs103182 | chr20 | CCAAGCCCTATGCCAAGGATATAACAAT (SEQ ID NO: 15) | ATGGGCTCACGGAAGAAGAACACAAAG (SEQ ID NO: 16) |
| rs1031825 | chr20 | GAGCATACTTGAAAGCAGTGATTATATC (SEQ ID NO: 17) | AGACAAAAACTGGAAAATATTTGAATTACC (SEQ ID NO: 18) |
| rs10488710 | chr11 | AAGGGTACTCATTAACCAAGTGTTTTA (SEQ ID NO: 19) | TCTGAAGCATGTTTCGCAAAGTGCAG (SEQ ID NO: 20) |
| rs10488710 | chr11 | GGGAACTCCTAATACAGTAAAACCTCT (SEQ ID NO: 21) | CACTAGATTTAAGTTCTTTCCTGATGTG (SEQ ID NO: 22) |
| rs10495407 | chr1 | GTTCTCCCAAATTTACATTGCCACTGA (SEQ ID NO: 23) | CAAGGATACCAAACCTGCAGGCATAAA (SEQ ID NO: 24) |
| rs1058083 | chr13 | ATGCCAGGCCAGCCACAGAGTGCC (SEQ ID NO: 25) | CAGAACCTTGAACCAGTGCATGGTTA (SEQ ID NO: 26) |
| rs10773760 | chr12 | ATCACTGTCCATCACGACACCGAGTG (SEQ ID NO: 27) | CCCTCCAGTGTTTTGGGTGGG (SEQ ID NO: 28) |
| rs10776839 | chr9 | TATGAACCCCAGCATGGGGCGGGGC (SEQ ID NO: 29) | TCTCTCTGGGATCATGTGAGGCGGGAA (SEQ ID NO:. 30) |
| rs1109037 | chr2 | GGGCTGAAAGATGATGGCAGAGC (SEQ ID NO: 31) | CCTCACCACCAGCTCTGTGACA (SEQ ID NO: 32) |
| rs1109037 | chr2 | GGACAGGTGCTTGGATGTCAGGGTGAA (SEQ ID NO: 33) | GTCCAACCAACAAGGATGTGGAGGAAT (SEQ ID NO: 34) |
| rs1294331 | chr1 | CTGGGGATGAACTCTCTTTGGAGTTT (SEQ ID NO: 35) | TTTGGAAGGGTTTTTCGTCTTGTTTAG (SEQ ID NO: 36) |
| rs12997453 | chr2 | TCATTTTTACCATTTAACAGCTCTGATG (SEQ ID NO: 37) | AGAATCACAGACTCTTACAGGTCCTAG (SEQ ID NO: 38) |
| rs12997453 | chr2 | TGAGTTTTTACCTACCTTTCTTGCACA (SEQ ID NO: 39) | AGTGCCTTAACAACAGCAAAATCTCTC (SEQ ID NO: 40) |
| rs13182883 | chr5 | TACCATGTCTCCCCAGGCTCTCCG (SEQ ID NO: 41) | CTCCTTAAAACATAGTCTGATACTTATCG (SEQ ID NO: 42) |
| rs13182883 | chr5 | AGGTGGGACAAAGGCAGGAAGAAAGTA (SEQ ID NO: 43) | GGCACACTTAATTTTAACAGAAGGAGG (SEQ ID NO: 44) |
| rs13218440 | chr6 | CACAGAGACATGAGGCATTTTCATGGA (SEQ ID NO: 45) | GTTTCAGTCCACAGCAGAAAAAGACTC (SEQ ID NO: 46) |
| rs13218440 | chr6 | GAGGTACAGCTCCCACTGCCTCTGAGT (SEQ ID NO: 47) | TTGCCCTTTTCATTGGACAACTAAAAA (SEQ ID NO: 48) |
| rs1335873 | chr13 | CTACTGCACGTGGATGATATGGTTTCT (SEQ ID NO: 49) | TTATGACATTCATCAAAATGAAATTGCCA (SEQ ID NO: 50) |
| rs1335873 | chr13 | AACAATACATACCTGCACCCTGCCCTT (SEQ ID NO: 51) | GAGAGTGACATCTAGGTTGTCATCTGA (SEQ ID NO: 52) |
| rs1336071 | chr6 | TTGAAAAAGCATCAGATTAAAACAAAGAT (SEQ ID NO: 53) | AGTTCAGCAAACACTATGCACTGATAAA (SEQ ID NO: 54) |
| rs1336071 | chr6 | CCTTTCTGTTTTGTCCATCTGAAATTC (SEQ ID NO: 55) | TAATGAAACATCTGAGTACTTTTTAGGTC (SEQ ID NO: 56) |
| rs1355366 | chr3 | GTGTCTTAAAACCCATGATTTTCTTGTG (SEQ ID NO: 57) | ATTTTCCTTCTTCTTGCAGCTTTGAGT (SEQ ID NO: 58) |
| rs1355366 | chr3 | AGGCCTCCAGTGGCTCTGAAATTCTCA (SEQ ID NO: 59) | TCTTCAGACCTGTAATGGGGCTATTTG (SEQ ID NO: 60) |
| rs1357617 | chr3 | CAGACCACTTCACCCTCTGTACTTTA (SEQ ID NO: 61) | GTTTGAGACACAATTCCCCCAGG (SEQ ID NO: 62) |
| rs1357617 | chr3 | CCCAAATTCAGCTTGGGAAGTCAAA (SEQ ID NO: 63) | AGATTTTGCTGTGAAAGTGAGTGTCTG (SEQ ID NO: 64) |

TABLE 4-continued

Target (primers) used in experimental setting.

| TARGET REGION NAME | CHROMOSOME | 5' SEQUENCE (FORWARD)* | 3' SEQUENCE (REVERSE)** |
|---|---|---|---|
| rs1360288 | chr9 | GTCACAGCTTCGCTTTGCTACTCTT (SEQ ID NO: 65) | GACGGCAGGTGGGGGTCACC (SEQ ID NO: 66) |
| rs1360288 | chr9 | CCTCCAGACCTGAAAGATGGAGGCTTT (SEQ ID NO: 67) | GTGTCCCCTCAATCCCCTCTCCATTT (SEQ ID NO: 68) |
| rs1382387 | chr16 | TGTAGAATTTGATTAAAGTGTCTTCTGGA (SEQ ID NO: 69) | GCTCTGTAACATCCTAAGGGATTTTTGCT (SEQ ID NO: 70) |
| rs1413212 | chr1 | GCCGACTTATTAGACGGACAGCATTTT (SEQ ID NO: 71) | AATGGAATGTTGCAGCTTGAACATAAT (SEQ ID NO: 72) |
| rs1454361 | chr14 | CTGGAACACATCAAAAACCACCATCTC (SEQ ID NO: 73) | GCCTCACCCAAAGGCAGACATAG (SEQ ID NO: 74) |
| rs1463729 | chr9 | ATACTTGGCTGTCTGGGAGCCTGTAG (SEQ ID NO: 75) | ATGGGCATACATGCATACACATGTGC (SEQ ID NO: 76) |
| rs1490413 | chr1 | ATGTTGGTGGAAGGGACTGAGAAGCCT (SEQ ID NO: 77) | TTTCTGTGCTGAGCATTTTATATGTGC (SEQ ID NO: 78) |
| rs1493232 | chr18 | TCACAGTGATCCATACACTAAAACAAG (SEQ ID NO: 79) | AGACTTTTGTTAAATTATCATCAAGGAGAT (SEQ ID NO: 80) |
| rs1498553 | chr11 | CCAGAGACCTGTTCTCTGTCCATTATT (SEQ ID NO: 81) | AATTGCAGCTGAGAGAAAACAGTAGTA (SEQ ID NO: 82) |
| rs1498553 | chr11 | GATCTATGGAAGTGCTGAGAAGGGAAG (SEQ ID NO: 83) | CGCTCACTCCCCTACAAATGTCAACAA (SEQ ID NO: 84) |
| rs1523537 | chr20 | TGGGTGAGACAATGCACAGAACTG (SEQ ID NO: 85) | AAAAAGCACTGGGATCCTCACTTTGG (SEQ ID NO: 86) |
| rs1523537 | chr20 | GATGCTATCGCTGGCTATTAGGTGATC (SEQ ID NO: 87) | ATACAGGTAGAGAGTGATGAAGCCAAG (SEQ ID NO: 88) |
| rs1528460 | chr15 | AGAGAGATTGATTATGTTGGGATGGGG (SEQ ID NO: 89) | TGCAGTTTGCTGAGTTTCACCAAATC (SEQ ID NO: 90) |
| rs159606 | chr5 | TGATCCACATTGTATGGTTTTAGGCA (SEQ ID NO: 91) | GTGCTTATTAGATGTTTGTGCTCACAA (SEQ ID NO: 92) |
| rs1736442 | chr18 | TTGATGTTTCTGTGTGTTGAGTGGGGG (SEQ ID NO: 93) | GGATCTGGCTGTTCCTTAGTTCATCAT (SEQ ID NO: 94) |
| rs1736442 | chr18 | AGAGCGCTTGTCTGAATGGAGAC (SEQ ID NO: 95) | CATTTTAAAGAAAAGAGGAGCTGGGTG (SEQ ID NO: 96) |
| rs1821380 | chr15 | CAGTGCAAGACAAGCGATTGAAAGAAG (SEQ ID NO: 97) | AAGGGACAAGGAAAGAGTGCTCCTTC (SEQ ID NO: 98) |
| rs188610 | chr13 | CCCAGTCTCCAAACCGCTGTAATATTT (SEQ ID NO: 99) | GCCCTTGTGCACATAGATGCAAAG (SEQ ID NO: 100) |
| rs1979255 | chr4 | ATGAGCAAGAGTTCCAACGTTCCATG (SEQ ID NO: 101) | TGAATCCAAAGGTGGATTCTCTAAGGC (SEQ ID NO: 102) |
| rs1979255 | chr4 | AAATTGAATCATAGCTTGTGTTGGTCAGG (SEQ ID NO: 103) | TTCTCAAAGGAAAGAAAAATATCAGTTCA (SEQ ID NO: 104) |
| rs2040411 | chr22 | CAGACCAACTTGGCTTTAACAGATGCA (SEQ ID NO: 105) | CACAAAAGAACTGGCATTCCAGAACT (SEQ ID NO: 106) |
| rs2046361 | chr4 | TGTATCCTTACCTTTAAGACTTTTCCTAT (SEQ ID NO: 107) | ATGCAAATATCAGTTTTGATGAAGCAA (SEQ ID NO: 108) |
| rs2046361 | chr4 | TGATCGTTCATAGACAATAGATACATACA (SEQ ID NO: 109) | GGCTTTCAAGCCTTTTCTGCAATGA (SEQ ID NO: 110) |
| rs2056277 | chr8 | CGTTCTGTATAGGCACCATATAGCACT (SEQ ID NO: 111) | ACGGATTGAATGAAGCAGCGGTCT (SEQ ID NO: 112) |

TABLE 4-continued

Target (primers) used in experimental setting.

| TARGET REGION NAME | CHROMO- SOME | 5' SEQUENCE (FORWARD)* | 3' SEQUENCE (REVERSE)** |
|---|---|---|---|
| rs2076848 | chr11 | AGACTTTTGGCTTAAATCAATGGG TCT (SEQ ID NO: 113) | TCATGGGAGTTTCTGATGTCACTAAG G (SEQ ID NO: 114) |
| rs2107612 | chr12 | ACCACTCACATGTCAAATAAAATA ACTG (SEQ ID NO: 115) | CTCCCACTGAACTTCATAAAAACAA AAGA (SEQ ID NO: 116) |
| rs2111980 | chr12 | TTATCCCTTTCCTGTCTGGGCTGA ATC (SEQ ID NO: 117) | GGGGGTTGGAGTGGGGCGGA (SEQ ID NO: 118) |
| rs214955 | chr6 | GTGCACATTCTAAGAACTGGTGAT TCT (SEQ ID NO: 119) | CCTTCAGGGATTTCCAGCAGTGG (SEQ ID NO: 120) |
| rs221956 | chr21 | TTTGGAGCTTGGTGATGAGTGGAG GCT (SEQ ID NO: 121) | AGACAACCATGAGCAGAATGCTGGT A (SEQ ID NO: 122) |
| rs2269355 | chr12 | TTCTGTTGTGGCTCGTCTTCCTGA GC (SEQ ID NO: 123) | GCCTCTGAGAGGGTAGGGACA (SEQ ID NO: 124) |
| rs2342747 | chr16 | ATCCAATGCTCAGGGGAGACATT AGCT (SEQ ID NO: 125) | TCCTATCTAATTCTTCTAATTTCTCGT CAA (SEQ ID NO: 126) |
| rs2399332 | chr3 | CCAGCATCTGTTGTTTTAACTTTCT TT (SEQ ID NO: 127) | AGAAGTATCTGTTCATGTATTTTGCT GA (SEQ ID NO: 128) |
| rs251934 | chr5 | CAAAGAACTGACCCTTGCAGAGA ACT (SEQ ID NO: 129) | GATTCTAGCAAGAGAATGCAGGTGC T (SEQ ID NO: 130) |
| rs279844 | chr4 | ACTCCAGAAGCTACTGGGATATTA ATTA (SEQ ID NO: 131) | GTTCATTAAGAAAACCTGTGACAAA CAT (SEQ ID NO: 132) |
| rs279844 | chr4 | TCTCTAAACTTCCTTGATATTAAC TACTGA (SEQ ID NO: 133) | ATACTTACCAGACTGCCTGCTTCTTA G (SEQ ID NO: 134) |
| rs2830795 | chr21 | GAACATAGTTCAAGGAGCTTACAG CCTC (SEQ ID NO: 135) | TGCAGCCTTCCTATTTACCGAAAGC (SEQ ID NO: 136) |
| rs2831700 | chr21 | CAGTCTGTGTAGCCAACACACACT AAT (SEQ ID NO: 137) | CCAATTTCCCAGCCTACATCAGCTAT T (SEQ ID NO: 138) |
| rs2920816 | chr12 | TAAACCTATTCCACTAACTTCAGG AAC (SEQ ID NO: 139) | AGTGTACCTGCAGAACTGTAGAGAA TC (SEQ ID NO: 140) |
| rs321198 | chr7 | CAGAAGTGGAATCACAAAAGGAA AACA (SEQ ID NO: 141) | AAATTGTAGGTGTGTAAGTGCATCTC T (SEQ ID NO: 142) |
| rs321198 | chr7 | CTCCTACACACAGGCTTCAGGTTA C (SEQ ID NO: 143) | ATTTTTCCCAGTCCCTTTACCAAAAA (SEQ ID NO: 144) |
| rs338882 | chr5 | TGTGCCTGTGCACACACACGTTTG G (SEQ ID NO: 145) | GCCAGGAGCGCAGCTCACGC (SEQ ID NO: 146) |
| rs338882 | chr5 | CAGCCGAAGAATCCAGCCCTTGT (SEQ ID NO: 147) | GACCTTTCCCCGCTCAGAGCTCCTTC A (SEQ ID NO: 148) |
| rs354439 | chr13 | AAAGAGGGGTGTTCTGGTGGCTTC TCTT (SEQ ID NO: 149) | CACCTCTTATCAGTACGCAGGCAAA (SEQ ID NO: 150) |
| rs354439 | chr13 | GTGATACATGAGAGAGATACATA AGGG (SEQ ID NO: 151) | TCCTCCCTGAAAATTATAGCAGGTCT (SEQ ID NO: 152) |
| rs3780962 | chr10 | ACGGGTGAAAGCTGATATCTTGAC CT (SEQ ID NO: 153) | GTAATTTGCCATCACTTTCAGTGGCA A (SEQ ID NO: 154) |
| rs3780962 | chr10 | TCAAAAACAAAGAAACATGGGAT GAAC (SEQ ID NO: 155) | CAGATCCATCATTGCCAGTAGACAA AC (SEQ ID NO: 156) |
| rs430046 | chr16 | CAAGAGGAGTCAAGGCATTTGAC CA (SEQ ID NO: 157) | TTGGCATTCAGCGGCCCCCAGA (SEQ ID NO: 158) |
| rs4364205 | chr3 | CATTCACCATTTGATAGCCATTTG GGT (SEQ ID NO: 159) | TGTAAGTAATTATACCATTTTACACT CCCA (SEQ ID NO: 160) |

TABLE 4-continued

Target (primers) used in experimental setting.

| TARGET REGION NAME | CHROMO-SOME | 5' SEQUENCE (FORWARD)* | 3' SEQUENCE (REVERSE)** |
|---|---|---|---|
| rs445251 | chr20 | GTTTTGATCACCAACCACTTGCAGTT (SEQ ID NO: 161) | GCCTGGACAACATGATGTCTCTATATTAAA (SEQ ID NO: 162) |
| rs445251 | chr20 | CACCTGGCCTACAATTCAAATTAATGT (SEQ ID NO: 163) | AGTTTGAATCAGAAATAAGATGTGAATGA (SEQ ID NO: 164) |
| rs4530059 | chr14 | ACTCCTGGGGATACAAGAGCTTCC (SEQ ID NO: 165) | TTATTGTCAGCGTTGTTTAAATTCTGG (SEQ ID NO: 166) |
| rs4530059 | chr14 | GAGGAAGCCGTTGCTGGTCTC (SEQ ID NO: 167) | ATCTCCAAGCTCAGCTCAGCCCAAGA (SEQ ID NO: 168) |
| rs4606077 | chr8 | AATCTGAGCTCGAGGTAGCAGGAA (SEQ ID NO: 169) | CAGGGAGGGCTTTGGTGTCTG (SEQ ID NO: 170) |
| rs4606077 | chr8 | GGCCTTGTGCTTTCACTGGGATGCAAAT (SEQ ID NO: 171) | GTGGGGAAAAGTGAGTGATTCGTGTT (SEQ ID NO: 172) |
| rs560681 | chr1 | CGTGACTCTCATATATCTGTGGAAGCA (SEQ ID NO: 173) | TCAGAAAGAAACTGGTGGGAACTCC (SEQ ID NO: 174) |
| rs576261 | chr19 | AGGCATTTTCTCTCATCTTGTTTGCA (SEQ ID NO: 175) | GGGAGGCACAAAAGAGGTTGATG (SEQ ID NO: 176) |
| rs6444724 | chr3 | GTTAGAAAGGAGAATCAGGAAATAGTCA (SEQ ID NO: 177) | CCTCTTTAATTTACTCAAGACTAATTAGCC (SEQ ID NO: 178) |
| rs6811238 | chr4 | TCAAAGCACCAGGCATTTGACCT (SEQ ID NO: 179) | GGCTATAAATTTGGCCTCTGTATCAACC (SEQ ID NO: 180) |
| rs6811238 | chr4 | ATTTTCATAGAAGTACTTCATTTGGCTAG (SEQ ID NO: 181) | TTCCCAACTATGGTGAAAGAAAATCAA (SEQ ID NO: 182) |
| rs6955448 | chr7 | TTCTTATGTAATCGTCATCCAACAAGA (SEQ ID NO: 183) | GGAGAGGATGGTGTGGGGAAAATAAAA (SEQ ID NO: 184) |
| rs7041158 | chr9 | GAAATACTTTCCCCAACAAGCAGTTT (SEQ ID NO: 185) | TGACAAAATAACAAGTTCCGTTTGATT (SEQ ID NO: 186) |
| rs717302 | chr5 | CGTTCACCACACAGTTAATACGATATGC (SEQ ID NO: 187) | TCTCTAGAACCTGCCAAATCACTTATT (SEQ ID NO: 188) |
| rs717302 | chr5 | ATAAAAGGATATGGCAAATAAGCTTTAGAA (SEQ ID NO: 189) | GATTGCTTGCCCACATTCCATTCAAAG (SEQ ID NO: 190) |
| rs719366 | chr19 | GATTGCTTGCCCACATTCCATTCAAAG (SEQ ID NO: 191) | GATTGCTTGCCCACATTCCATTCAAAG (SEQ ID NO: 192) |
| rs719366 | chr19 | GATTGCTTGCCCACATTCCATTCAAAG (SEQ ID NO: 193) | GATTGCTTGCCCACATTCCATCAAAG (SEQ ID NO: 194) |
| rs722098 | chr21 | GATTGCTTGCCCACATTCCATTCAAAG (SEQ ID NO: 195) | GATTGCTTGCCCACATTCCATTCAAAG (SEQ ID NO: 196) |
| rs722290 | chr14 | GATTGCTTGCCCACATTCCATTCAAAG (SEQ ID NO: 197) | GATTGCTTGCCCACATTCCATTCAAAG (SEQ ID NO: 198) |
| rs727811 | chr6 | GATTGCTTGCCCACATTCCATTCAAAG (SEQ ID NO: 199) | GATTGCTTGCCCACATTCCATTCAAAG (SEQ ID NO: 200) |
| rs727811 | chr6 | ATGATTGTAAGTCGTTGAAGTTCCGG (SEQ ID NO: 201) | AAAGAACATACTTTGGCTCATTCTGGT (SEQ ID NO: 202) |
| rs729172 | chr16 | CTGAGATCCCTTTGATAGCGCTTTCTA (SEQ ID NO: 203) | CATATTTCCTCAATATAAATTCTAACACGC (SEQ ID NO: 204) |
| rs733164 | chr22 | TAGGGGTTGAGTCCATGCCAAGACAA (SEQ ID NO: 205) | ACCACATCCCCAATTAGAGTCAAGAA (SEQ ID NO: 206) |
| rs733164 | chr22 | CTTGCCAAAGAAAACTCAAGCGAGG (SEQ ID NO: 207) | GGGGGCACTTCTGAAGGGGACTGTGTT (SEQ ID NO: 208) |

TABLE 4-continued

Target (primers) used in experimental setting.

| TARGET REGION NAME | CHROMOSOME | 5' SEQUENCE (FORWARD)* | 3' SEQUENCE (REVERSE)** |
|---|---|---|---|
| rs735155 | chr10 | AAAAAGAAGGTCGACGCCGGCTC CAGAAGG (SEQ ID NO: 209) | CGACTAGCCCGGTTTCCCAAGA (SEQ ID NO: 210) |
| rs735155 | chr10 | CTCTCCGGTTTTCTCCAGGTTAGG T (SEQ ID NO: 211) | GACAGCAAACATGGACAAACCCTA TC (SEQ ID NO: 212) |
| rs737681 | chr7 | TTACTGTGATGTAGGCACTGTTCC AG (SEQ ID NO: 213) | AGAGAGGTCTCAGGGCCCAAGCCAT C (SEQ ID NO: 214) |
| rs740598 | chr10 | ATTGTCCTCCTTGAGATGTGGCTT CC (SEQ ID NO: 215) | CCATTACCTGAGAAGGCATTTCTAA AG (SEQ ID NO: 216) |
| rs740598 | chr10 | CCGGTTCATTAATAAGACGGGAC ATCC (SEQ ID NO: 217) | GGGTTTCATGTTATGGAGAAAAACA AC (SEQ ID NO: 218) |
| rs740910 | chr17 | CCCTTTCTCTGTTCATAGGCAAAC ACA (SEQ ID NO: 219) | TCTAACTCATTCTTTTTAACAGCTGC G (SEQ ID NO: 220) |
| rs763869 | chr8 | CAGCCAAACCATATCAAGTGGTT CTG (SEQ ID NO: 221) | TGTTTGTAATTGATTTTGTTACTCTTT GG (SEQ ID NO: 222) |
| rs8037429 | chr15 | AAATGTATACATTATTTGCTGAAA AGTGC (SEQ ID NO: 223) | TGATAAATGTTGAAGCCTACACTGA AG (SEQ ID NO: 224) |
| rs8078417 | chr17 | AACCTCTGTGTTCTGAGCCACGTG (SEQ ID NO: 225) | TAGCTGCTTCAGCCTGGTGGTCTGGG (SEQ ID NO: 226) |
| rs8078417 | chr17 | TCCTTGAGGCTCTTCTCACACTCA GAT (SEQ ID NO: 227) | AATATGACTGGAGTTCATCTGTGTGC C (SEQ ID NO: 228) |
| rs826472 | chr10 | TCTGCTATCCTGATGAGAGATAGG T (SEQ ID NO: 229) | TTTCTCAAATACACAAAAGAGTTTAC CAA (SEQ ID NO: 230) |
| rs826472 | chr10 | TGATGCTGAATTTTGTCTCTGTTAT ATTAG (SEQ ID NO: 231) | TTTTCCTCTTGATCCCTATATTGCCT (SEQ ID NO: 232) |
| rs873196 | chr14 | TCTCTCTGGTTCACAAATGAGCAT GC (SEQ ID NO: 233) | GCTGCCATTTTCTTCCAGGAAGTAT C (SEQ ID NO: 234) |
| rs873196 | chr14 | ACTCCAACTCCTGCCAGCCTT (SEQ ID NO: 235) | GGCCAGCCTGACTAACATGGCAAAA T (SEQ ID NO: 236) |
| rs876724 | chr2 | GTTGTTTAAACATTTTAAACCATG AGAAGT (SEQ ID NO: 237) | TGCATGATGATTCCCCTGCCAA (SEQ ID NO: 238) |
| rs876724 | chr2 | TCAAATTTAGTAGATGTAGACAGA CTCC (SEQ ID NO: 239) | GACTGTTCTCTGGCTTAAGATTTATT TAGG (SEQ ID NO: 240) |
| rs891700 | chr1 | TTTCTTGTGTCTTCAATCACTTCTT ATTTT (SEQ ID NO: 241) | AAGTGTACAAAACTCCATGTACCAG GT (SEQ ID NO: 242) |
| rs901398 | chr11 | AGAGGCAACGCCACCATCATACA GAC (SEQ ID NO: 243) | ATGGCTGTCCTCCTGGATGGTAAATA (SEQ ID NO: 244) |
| rs907100 | chr2 | CGAAAAGGTGAAACCAGTCCTCTT TTG (SEQ ID NO: 245) | AGAATCGTTATCAGGAACTCCCTGG GC (SEQ ID NO: 246) |
| rs914165 | chr21 | TATAAATCACGGAGTGCAGACCA GTCACCT (SEQ ID NO: 247) | AGGGTCCCGTGTGATCATCATTGTAT C (SEQ ID NO: 248) |
| rs914165 | chr21 | CTGAGCCCGCCCCCACCCAGTGCA AAA (SEQ ID NO: 249) | TCTGTGAAAGTTTCTGTTCTCTCTCT C (SEQ ID NO: 250) |
| rs917118 | chr7 | AGAAGCTTGAGCAAAGGCCTTGA GAT (SEQ ID NO: 251) | CTAAAGGGCAGGTGCCAGCTG (SEQ ID NO: 252) |
| rs938283 | chr17 | TCTTCTCTTAGAAGGACACTGGTC AGA (SEQ ID NO: 253) | CCATAATAGAAGGGTGCACGGGAAT TT (SEQ ID NO: 254) |
| rs964681 | chr10 | GCCGGGGACTTTGACTATTAAATG AAC (SEQ ID NO: 255) | CAGGTACCTTCCTGACGCCCA (SEQ ID NO: 256) |

TABLE 4-continued

Target (primers) used in experimental setting.

| TARGET REGION NAME | CHROMO-SOME | 5' SEQUENCE (FORWARD)* | 3' SEQUENCE (REVERSE)** |
|---|---|---|---|
| rs987640 | chr22 | GCTGTTTAAGGGTAAAGGGGTAG TTACT (SEQ ID NO: 257) | GGAGTAGCTTTCAATTATTTTGGAGC C (SEQ ID NO: 258) |
| rs987640 | chr22 | GACTTAATACAGACGATGGCATG GGCT (SEQ ID NO: 259) | GAGTGCATAGCTCTCATGGAAAAAG TC (SEQ ID NO: 260) |
| rs9905977 | chr17 | ATGACAATGATCTTAGGGCCACG AG (SEQ ID NO: 261) | TAGTCGAGGGAGGCTGCTCTCAG (SEQ ID NO: 262) |
| rs9905977 | chr17 | CTTTGTCCCTCAGGCTTGGCC (SEQ ID NO: 263) | AAGAGGATAGGCTAACTGACTGCCT T (SEQ ID NO: 264) |
| rs993934 | chr2 | CAGTTTGCACTAAATGATTACAGG TTA (SEQ ID NO: 265) | ATAAACACTAACATGTAACATTGCT AGAG (SEQ ID NO: 266) |
| rs993934 | chr2 | ACAGTCTCCAGAGTATATTAGCTT AGTTC (SEQ ID NO: 267) | CATTCATGAACTTAGTTGGCAATTAA ATT (SEQ ID NO: 268) |
| rs9951171 | chr18 | CGAGCTCAATTTTCTTGTCCCTGC TTT (SEQ ID NO: 269) | ACTTACTGTTGTGTGCAGTCCAAGC (SEQ ID NO: 270) |

*by convention, all sequences are reported as 5'→3';
**For CPR amplification of the designated Target Regions, the 3' Sequences listed in the REVERSE column are converted to the reverse complement of the sequence and primers are synthesized which have a sequence which is the reverse complement of the 3' Sequences listed.

Synthetic Study Design

SNP Panel Validation

Using Minor Allele Frequency (MAF) in general population reported in 1000Genome (1000G) project to calculate the probability of mutation of each allele of each of the 94 SNPs in our panel (Table 3), we created 10000 simulated genotypes (0/0, 0/1, 1/1), under the hypothesis of independence of mutation between SNPs:

$$p(snp1=0/1, snp2=0/1)=p(snp1=0/1)p(snp2=0/1)$$

that is the joint probability of the presence of two SNPs is equal to the product of the single probability.

Calculations were made for each SNP in each simulated sample as:

$$p(SNP_i=0/0)=p(AF(SNP_i)) \times p(MAF1000G(SNP_i))$$
where $AF(SNP_i=0/0)=0$ $$p(SNP_i=0/1)=p(AF(SNP_i)) \times p(MAF1000G(SNP_i))$$
where $AF(SNP_i=0/1)=0.5$ $$p(SNP_i=1/1)=p(AF(SNP_i)) \times p(MAF1000G(SNP_1))^2$$
where $AF(SNP_i=1/1)=1$ Our aim was to estimate the probability of each SNP to be mutated in the simulated population, in a genotype useful for our evaluation.

TABLE 5

SNPs list, 1000G MAF and calculated frequencies according to the formula above.

| LOCUS | CHROMOSOME POSITION HG19 | MAF 1000G | P0/0 | P0/1 | P1/1 |
|---|---|---|---|---|---|
| rs10495407 | 238439308 | A = 0.2410/1207 | 0.58 | 0.37 | 0.06 |
| rs1294331 | 233448413 | T = 0.4207/2107 | 0.34 | 0.49 | 0.18 |
| rs1413212 | 242806797 | T = 0.3654/1830 | 0.40 | 0.46 | 0.13 |
| rs1490413 | 4367323 | G = 0.4994/2501 | 0.25 | 0.50 | 0.25 |
| rs560681 | 160786670 | G = 0.3373/1689 | 0.44 | 0.45 | 0.11 |
| rs891700 | 239881926 | A = 0.4936/2472 | 0.26 | 0.50 | 0.24 |
| rs1109037 | 10085722 | A = 0.4395/2201 | 0.31 | 0.49 | 0.19 |
| rs12997453 | 182413259 | A = 0.3516/1761 | 0.42 | 0.46 | 0.12 |
| rs876724 | 114974 | T = 0.2724/1364 | 0.53 | 0.40 | 0.07 |
| rs907100 | 239563579 | G = 0.4117/2062 | 0.35 | 0.48 | 0.17 |
| rs993934 | 124109213 | G = 0.4147/2077 | 0.34 | 0.49 | 0.17 |
| rs1355366 | 190806108 | C = 0.4046/2026 | 0.35 | 0.48 | 0.16 |
| rs1357617 | 961782 | A = 0.2240/1122 | 0.60 | 0.35 | 0.05 |
| rs2399332 | 110301126 | T = 0.3484/1745 | 0.42 | 0.45 | 0.12 |
| rs4364205 | 32417644 | T = 0.3752/1879 | 0.39 | 0.47 | 0.14 |
| rs6444724 | 193207380 | C = 0.4667/2337 | 0.28 | 0.50 | 0.22 |
| rs1979255 | 190318080 | C = 0.3918/1962 | 0.37 | 0.48 | 0.15 |
| rs2046361 | 10969059 | A = 0.4307/2157 | 0.32 | 0.49 | 0.19 |
| rs279844 | 46329655 | T = 0.4647/2327 | 0.29 | 0.50 | 0.22 |
| rs6811238 | 169663615 | T = 0.4415/2211 | 0.31 | 0.49 | 0.19 |
| rs13182883 | 136633338 | A = 0.4157/2082 | 0.34 | 0.49 | 0.17 |
| rs159606 | 17374898 | A = 0.3438/1722 | 0.43 | 0.45 | 0.12 |
| rs251934 | 174778678 | G = 0.2678/1341 | 0.54 | 0.39 | 0.07 |
| rs338882 | 178690725 | G = 0.4561/2284 | 0.30 | 0.50 | 0.21 |
| rs717302 | 2879395 | G = 0.3726/1866 | 0.39 | 0.47 | 0.14 |
| rs13218440 | 12059954 | A = 0.4123/2065 | 0.35 | 0.48 | 0.17 |
| rs1336071 | 94537255 | T = 0.4209/2108 | 0.34 | 0.49 | 0.18 |
| rs214955 | 152697706 | C = 0.4708/2358 | 0.28 | 0.50 | 0.22 |
| rs727811 | 165045334 | T = 0.4878/2443 | 0.26 | 0.50 | 0.24 |
| rs321198 | 137029838 | T = 0.4365/2186 | 0.32 | 0.49 | 0.19 |
| rs6955448 | 4310365 | T = 0.3193/1599 | 0.46 | 0.43 | 0.10 |
| rs737681 | 155990813 | T = 0.3600/1803 | 0.41 | 0.46 | 0.13 |
| rs917118 | 4457003 | T = 0.4427/2217 | 0.31 | 0.49 | 0.20 |
| rs10092491 | 28411072 | T = 0.3844/1925 | 0.38 | 0.47 | 0.15 |
| rs2056277 | 139399116 | T = 0.1579/791 | 0.71 | 0.27 | 0.02 |
| rs4606077 | 144656754 | T = 0.3337/1671 | 0.44 | 0.44 | 0.11 |
| rs763869 | 1375610 | G = 0.4131/2069 | 0.34 | 0.48 | 0.17 |
| rs1015250 | 1823774 | C = 0.4285/2146 | 0.33 | 0.49 | 0.18 |
| rs10776839 | 137417308 | T = 0.4062/2034 | 0.35 | 0.48 | 0.16 |
| rs1360288 | 128968063 | T = 0.3243/1624 | 0.46 | 0.44 | 0.11 |
| rs1463729 | 126881448 | C = 0.4143/2075 | 0.34 | 0.49 | 0.17 |

TABLE 5-continued

SNPs list, 1000G MAF and calculated frequencies according to the formula above.

| LOCUS | CHROMOSOME POSITION HG19 | MAF 1000G | P0/0 | P0/1 | P1/1 |
|---|---|---|---|---|---|
| rs7041158 | 27985938 | T = 0.3770/1888 | 0.39 | 0.47 | 0.14 |
| rs3780962 | 17193346 | A = 0.4978/2493 | 0.25 | 0.50 | 0.25 |
| rs735155 | 3374178 | C = 0.4613/2310 | 0.29 | 0.50 | 0.21 |
| rs740598 | 118506899 | G = 0.3686/1846 | 0.40 | 0.47 | 0.14 |
| rs826472 | 2406631 | T = 0.2486/1245 | 0.56 | 0.37 | 0.06 |
| rs964681 | 132698419 | C = 0.3415/1710 | 0.43 | 0.45 | 0.12 |
| rs10488710 | 115207176 | C = 0.3676/1841 | 0.40 | 0.46 | 0.14 |
| rs1498553 | 5709028 | C = 0.4938/2473 | 0.26 | 0.50 | 0.24 |
| rs2076848 | 134667546 | T = 0.3347/1676 | 0.44 | 0.45 | 0.11 |
| rs901398 | 11096221 | C = 0.3361/1683 | 0.44 | 0.45 | 0.11 |
| rs10773760 | 130761696 | G = 0.3514/1760 | 0.42 | 0.46 | 0.12 |
| rs2107612 | 888320 | G = 0.2883/1444 | 0.51 | 0.41 | 0.08 |
| rs2111980 | 106328254 | C = 0.4421/2214 | 0.31 | 0.49 | 0.20 |
| rs2269355 | 6945914 | G = 0.49 | 0.26 | 0.50 | 0.24 |
| rs2920816 | 40863052 | G = 0.3480/1743 | 0.43 | 0.45 | 0.12 |
| rs1058083 | 100038233 | A = 0.3888/1947 | 0.37 | 0.48 | 0.15 |
| rs1335873 | 20901724 | T = 0.4653/2330 | 0.29 | 0.50 | 0.22 |
| rs1886510 | 22374700 | A = 0.2606/1305 | 0.55 | 0.39 | 0.07 |
| rs354439 | 106938411 | A = 0.4838/2423 | 0.27 | 0.50 | 0.23 |
| rs1454361 | 25850832 | A = 0.4129/2068 | 0.34 | 0.48 | 0.17 |
| rs4530059 | 104769149 | A = 0.3121/1563 | 0.47 | 0.43 | 0.10 |
| rs722290 | 53216723 | C = 0.4986/2497 | 0.25 | 0.50 | 0.25 |
| rs873196 | 98845531 | C = 0.2234/1119 | 0.60 | 0.35 | 0.05 |
| rs1528460 | 55210705 | T = 0.4758/2383 | 0.27 | 0.50 | 0.23 |
| rs1821380 | 39313402 | G = 0.3966/1986 | 0.36 | 0.48 | 0.16 |
| rs8037429 | 53616909 | T = 0.4501/2254 | 0.30 | 0.50 | 0.20 |
| rs1382387 | 80106361 | C = 0.3912/1959 | 0.37 | 0.48 | 0.15 |
| rs2342747 | 5868700 | A = 0.3403/1704 | 0.44 | 0.45 | 0.12 |
| rs430046 | 78017051 | T = 0.3510/1758 | 0.42 | 0.46 | 0.12 |
| rs729172 | 5606197 | T = 0.2582/1293 | 0.55 | 0.38 | 0.07 |
| rs740910 | 5706623 | G = 0.1739/871 | 0.68 | 0.29 | 0.03 |
| rs8078417 | 80461935 | T = 0.3095/1550 | 0.48 | 0.43 | 0.10 |
| rs938283 | 77468498 | T = 0.5 | 0.25 | 0.50 | 0.25 |
| rs9905977 | 2919393 | A = 0.3259/1632 | 0.45 | 0.44 | 0.11 |
| rs1024116 | 75432386 | T = 0.3333/1669 | 0.44 | 0.44 | 0.11 |
| rs1493232 | 1127986 | C = 0.4671/2339 | 0.28 | 0.50 | 0.22 |
| rs1736442 | 55225777 | T = 0.3708/1857 | 0.40 | 0.47 | 0.14 |
| rs9951171 | 9749879 | A = 0.4455/2231 | 0.31 | 0.49 | 0.20 |
| rs576261 | 39559807 | C = 0.4389/2198 | 0.31 | 0.49 | 0.19 |
| rs719366 | 28463337 | G = 0.2628/1316 | 0.54 | 0.39 | 0.07 |
| rs1005533 | 39487110 | A = 0.4387/2197 | 0.32 | 0.49 | 0.19 |
| rs1031825 | 4447483 | A = 0.4453/2230 | 0.31 | 0.49 | 0.20 |
| rs1523537 | 51296162 | C = 0.4491/2249 | 0.30 | 0.49 | 0.20 |
| rs445251 | 15124933 | G = 0.4155/2081 | 0.34 | 0.49 | 0.17 |
| rs221956 | 43606997 | T = 0.3658/1832 | 0.40 | 0.46 | 0.13 |
| rs2830795 | 28608163 | G = 0.2831/1418 | 0.51 | 0.41 | 0.08 |
| rs2831700 | 29679687 | G = 0.3908/1957 | 0.37 | 0.48 | 0.15 |
| rs722098 | 16685598 | A = 0.4972/2490 | 0.25 | 0.50 | 0.25 |
| rs914165 | 42415929 | G = 0.4850/2429 | 0.27 | 0.50 | 0.24 |
| rs1028528 | 48362290 | G = 0.4417/2212 | 0.31 | 0.49 | 0.20 |
| rs2040411 | 47836412 | G = 0.4034/2020 | 0.36 | 0.48 | 0.16 |
| rs733164 | 27816784 | A = 0.2845/1425 | 0.51 | 0.41 | 0.08 |
| rs987640 | 33559508 | T = 0.4884/2446 | 0.26 | 0.50 | 0.24 |

MAF is the allele frequency of the minor represented base variant in the position of each SNP in a sequenced population.
P(SNP) in the population was calculated according the Hardy Weinberg Theory as:
p(0/0) = (1 − MAF1000G)$^2$
p(0/1) = 2 × (1 − MAF1000G) × MAF1000G
p(1/1) = MAF1000G$^2$ Limit of Detection: In Silico Evaluation We created 10 simulation FASTQ files mimicking the characteristics (coverage, quality, error rate) of the raw files coming from the Miseq Illumina instrument, using Simulvar v1.0 tool. The choice of the features was to cover the spectrum of possible output of the instrument (low coverage, high error rate to high coverage, low error rate). From the 10 initial files we created 5 pairs of BAM files with the 94 SNPs genotype obtained from 5 (randomized) of the 10000 genotypes simulated from general population allele frequency. The aim was to mimic the different concentrations (in a known percentage between 0.1% and 5%) of donor in recipient cfDNA.

Obtained files were analyzed using the analysis algorithm disclosed above.

Limit of Detection: In Vitro Evaluation

In order to confirm the previous result, we created 6 control samples, with a predefined quantity of individual 1 cfDNA in an amount individual 2 (1%, 5%, 10%, 25%, 50%, 100%), to test the limits of detection of our test methodology in a calculated, progressively diluted mixture of real couples of cfDNA samples.

Pilot Study Design

An early stage pilot study was performed on 23 sample series from heart transplanted patients undergoing EMB monitoring, to confirm the concept and check results. We tested the efficacy to precisely detect cfDNA of the donor (individual 1) in recipient (individual 2) blood.

Currently we developed an operating lab prototype, based on the specific designed genetic markers panel and the innovative algorithm.

Panel Design Validation

The process works correctly individuating the genomarker of the individual 1/individual 2 pair of cfDNA. In particular the probability to individuate at least one SNP with an informative genotype is reported in Table 6 and it is a probability near 1 both in case of homozygosis (0/0 and 1/1) and in case of heterozygosis (0/1 and 0/0).

As for design of the panel, at least the presence of 1 SNP genotype informative combination is sufficient to discriminate the DNA of different individuals.

TABLE 6

Probability of incidence of paired genotypes in a simulated 10000 individual population.

| Genotype individual 1 | Genotype individual 2 | Probability of incidence |
|---|---|---|
| 0/0 | 1/1 | 0.9999 |
| 0/0 | 0/1 | 0 9945 |
| 0/1 | 0/0 | 0.9945 |
| 1/1 | 0/0 | 0.9999 |

0/0 reference homozygous, 1/1 alternative homozygous, 0/1 or 1/0 heterozygous

Limit of Detection: In Silico Evaluation

Figure 3:
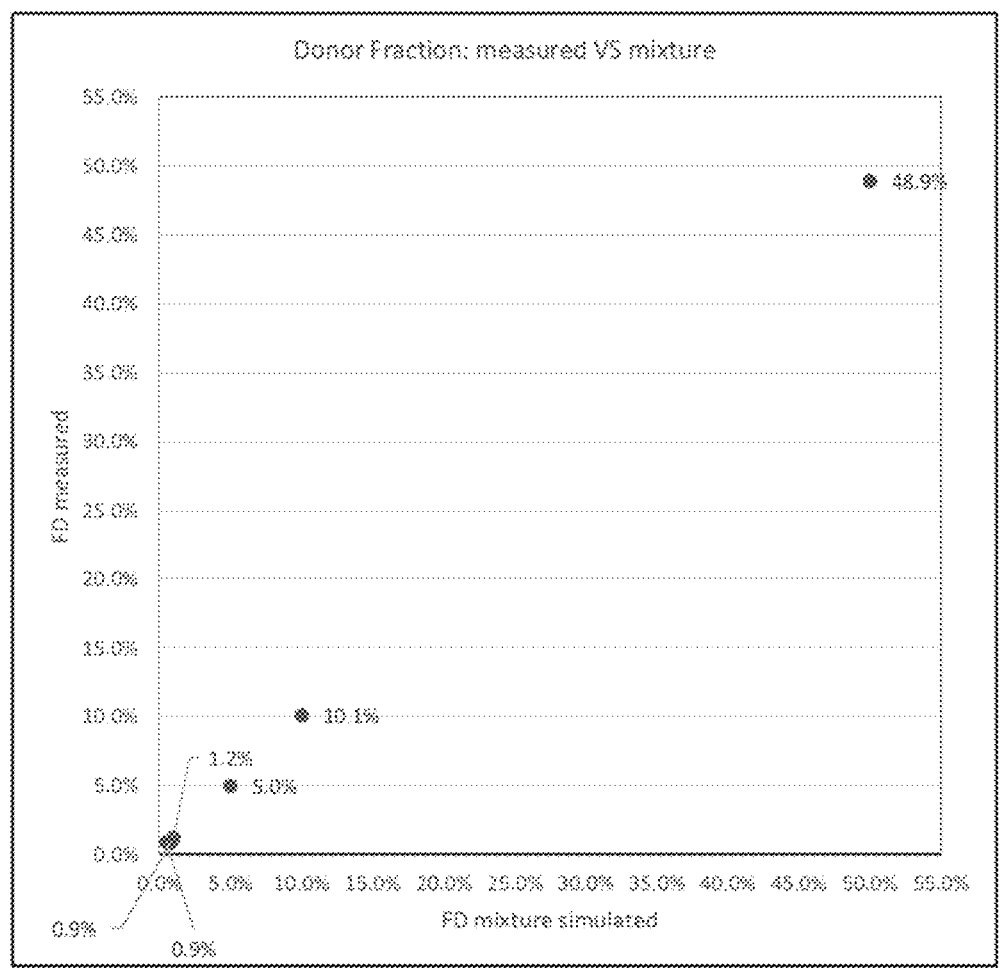
FIG. 3 shows the results of the simulation of a mixture of cfDNA different fractions in 2 different individuals (simulated donor and simulated receiver).

We identified a limit of detection of 1% of the developed method (minimum quantity of individual 1 cfDNA we can identify in the total of cfDNA, containing individual 1+individual 2 cfDNA). In real samples, we expect an increase of the donor DNA fraction within the total cfDNA concurrent with the presence of rejection and proportional to the degree of rejection. Table 7 and FIG. 3 represent the results of this evaluation. Statistics reported refers to the capacity of the algorithm to correctly identify SNPs in the reported fraction of donor DNA.

TABLE 7

Results of simulation of different concentrations of individual 1 and 2: statistics and 94 SNP.

| Concentration | Sample ID | DETECTION RATE | SENSITIVITY (TP RATE) | MISSING RATE (FN RATE) |
|---|---|---|---|---|
| 0.50% | couple 1 | 82.89% | 82.89% | 17.11% |
| | couple 2 | 72.97% | 72.97% | 27.03% |
| | couple 3 | 84.00% | 84.00% | 16.00% |
| | couple 4 | 78.05% | 78.05% | 21.95% |
| | couple 5 | 80.25% | 80.25% | 19.75% |
| 0.80% | couple 1 | 89.19% | 89.19% | 10.81% |
| | couple 2 | 89.19% | 89.19% | 10.81% |
| | couple 3 | 90.67% | 90.67% | 9.33% |
| | couple 4 | 89.02% | 89.02% | 10.98% |
| | couple 5 | 92.59% | 92.59% | 7.41% |
| 1% | couple 1 | 98.68% | 98.68% | 1.32% |
| | couple 2 | 98.65% | 98.65% | 1.35% |
| | couple 3 | 96.00% | 96.00% | 4.00% |
| | couple 4 | 97.56% | 97.56% | 2.44% |
| | couple 5 | 98.77% | 98.77% | 1.23% |
| 5% | couple 1 | 98.68% | 98.68% | 1.32% |
| | couple 2 | 98.65% | 98.65% | 1.35% |
| | couple 3 | 98.67% | 98.67% | 1.33% |
| | couple 4 | 98.78% | 98.78% | 1.22% |
| | couple 5 | 98.77% | 98.77% | 1.23% |
| 10% | couple 1 | 98.68% | 98.68% | 1.32% |
| | couple 2 | 98.65% | 98.65% | 1.35% |
| | couple 3 | 98.67% | 98.67% | 1.33% |
| | couple 4 | 98.78% | 98.78% | 1.22% |
| | couple 5 | 98.77% | 98.77% | 1.23% |
| 50% | couple 1 | 98.68% | 98.68% | 1.32% |
| | couple 2 | 98.65% | 98.65% | 1.35% |
| | couple 3 | 98.67% | 98.67% | 1.33% |
| | couple 4 | 98.78% | 98.78% | 1.22% |
| | couple 5 | 98.77% | 98.77% | 1.23% |

DETECTION RATE: % of variant identified on the total 94 SNP panel;
SENSITIVITY: rate of true positive identified on the total of called positive;
MISSING RATE: number of false negative in the total of called negative by the algorithm.

Limit of Detection: In Vitro Evaluation

We identified a limit of detection of 1% (minimum quantity of individual 2 cfDNA we can identify in the total of individual 1 cfDNA), coherent with simulated results. Limit of the evaluation was the technical difficulty of preparing the samples with a concentration <1%. Results are reported in FIG. 4. The algorithm was able to identify the correct individual 2 fraction in in vitro mixture, with an error of 0.01%.

Machine Learning Process Results for Prediction of Donor Genotype GT

To test the method accuracy and performance we used a machine learning supervised approach (Naïve Bayes) on simulated data as training set and real data (with known donor GT for each SNP in the panel) as test set. In Table 8 are reported results of the performance of the trained model.

FIG. 5 shows ROC (Receiver Operating Characteristic) curve, area under the curve was 0.991.

TABLE 8

Real GT VS GT predicted by the trained machine learning model.

| | Predicted GT | | |
|---|---|---|---|
| Real GT | 0/0 | 0/1 | 1/1 |
| 0/0 | 95.7% | 2.5% | 0% |
| 0/1 | 3.0% | 97% | 3.7% |
| 1/1 | 1.2% | 0.5% | 96.3% |

Finally, we applied the machine learning trained model on synthetic dataset (unknown donor GT, but known donor cfDNA fraction).

In Table 9 are reported results of the machine learning model.

TABLE 9

Donor fraction percentage calculated using GT predicted by the trained machine learning model on the synthetic dataset VS known percentage for same samples.

| | Expected Donor Fraction | Calculated Donor Fraction |
|---|---|---|
| Sample 1 | 0% | 3% |
| Sample 2 | 5% | 8% |
| Sample 3 | 10% | 10% |
| Sample 4 | 25% | 24% |
| Sample 5 | 50% | 35% |
| Sample 6 | 100% | 67% |

Early Stage Pilot Study

To test our pipeline in a real setting, gold standard results (derived from endomyocardial biopsy EMB) classified according to ISLHT standards (Stewart S, et al. Revision of the 1990 working formulation for the standardization of nomenclature in the diagnosis of heart rejection. J Heart Lung Transplant. 2005; 24:1710-20) were compared with our test in a cohort of 4 sample, in which donor blood were genotyped and donor GT used to calculate expected donor fraction. Calculated donor fraction was estimated using donor genotype inference using machine learning.

In Table 10 are reported Donor Fraction percentage calculated from the algorithm, preliminary classification and comparison with gold standard.

TABLE 10

Donor fraction calculated with known GT and calculated GT on a real dataset.

| | Expected Donor Fraction % | Calculated Donor Fraction % | EMB classification |
|---|---|---|---|
| Sample 1 | 27% | 19% | 3R |
| Sample 2 | 22% | 20% | 2R |
| Sample 3 | 27% | 24% | 3R |
| Sample 4 | 16% | 13% | 1R |

Finally, we applied our test on a cohort of 4 samples. Donor genomic DNA was not available, and we used the machine learning approach to calculate donor genotype. Donor fraction was then calculated with inferenced donor genotype. Results of the test and comparison with gold standard is reported in FIG. 6. For each patient 2 samples were collected, T0 after 15 days and T1 after 21 days from heart transplant.

CONCLUSIONS

Our system is useful to identify and measure correctly cfDNA of an individual in the total cfDNA extracted from a blood sample of another individual, starting from a percentage of 1% of concentration, with a very high sensitivity (98%).

In the hypothesis of transplant, our system can recognize the presence of unrelated donor cfDNA in the total amount sampled from the receiver and quantify it in order to identify the presence of rejection.

It can be used also to monitor during time after transplant the rejection, and the immunosuppressive therapy efficacy.

REFERENCES

1. Miller C A, Fildes J E, Ray S G, Doran H, Yonan N, Williams S G, Schmitt M. Non-invasive approaches for the diagnosis of acute cardiac allograft rejection. Heart. 2013 April; 99(7):445-53.
2. Costanzo M R, Dipchand A, Starling R, et al. The International Society of Heart and Lung Transplantation Guidelines for the care of heart transplant recipients. J Heart Lung Transplant. 2010; 29: 914-956.
3. Saraiva F, Matos V, Gonçalves L, Antunes M, Providência L. Complications of endomyocardial biopsy in heart transplant patients: A retrospective study of 2117 consecutive procedures. Transplant Proc. 2011; 43:1908-1912.
4. Stehlik J, Starling R C, Movsesian M A et al. Utility of longterm surveillance endomyocardial biopsy: a multiinstitutional analysis. J Heart Lung Transplant 2006; 25(12):1402-1409.)
5. Deckers J W, Hare J M, Baughman K L. Complications of transvenous right ventricular endomyocardial biopsy in adult patients with cardiomyopathy: a seven-year survey of 546 consecutive diagnostic procedures in a tertiary referral center. J Am Coll Cardiol 1992; 19(1): 43-47.
6. Pophal S G, Sigfusson G, Booth K L et al. Complications of endomyocardial biopsy in children. J Am Coll Cardiol 1999; 34(7):2105-2110
7. De Vlaminck I, Valantine H A, Snyder T M, et al. Circulating cell-free DNA enables noninvasive diagnosis of heart transplant rejection. Sci Transl Med. 2014; 6:241ra77.
8. Snyder T M, Khush K K, Valantine H A, Quake S R. Universal noninvasive detection of solid organ transplant rejection. Proc Natl Acad Sci USA. 2011; 108: 6229-34.
9. Oellerich M, Kanzow P, Beck J, et al. Graft-derived cell-free DNA (GcfDNA) as a sensitive measure of individual graft integrity after liver transplantation. Am J Transplant. 2014; 14(suppl 1):874.
10. Sigdel T K, Vitalone M J, Tran T Q, et al. A rapid noninvasive assay for the detection of renal transplant injury. Transplantation. 2013; 96:97-101.
11. Beck J, Bierau S, Balzer S, et al. Digital droplet PCR for rapid quantification of donor DNA in the circulation of transplant recipients as a potential universal biomarker of graft injury. Clin Chem. 2013; 59:1732-1741.
12. Grskovic M et al. Validation of a Clinical-Grade Assay to Measure Donor-Derived Cell-Free DNA in Solid Organ Transplant Recipients. J Mol Diagn. 2016; 18:890-902.
13. Gordon P M, et al. An Algorithm Measuring Donor Cell-Free DNA in Plasma of Cellular and Solid Organ Transplant Recipients That Does Not Require Donor or Recipient Genotyping. Front Cardiovasc Med. 2016; 3:33. eCollection 2016.
14. Pakstis A J, et al. SNPs for a universal individual identification panel. Hum Genet. 2010; 127:315-24.
15. Kidd K K, et al. Expanding data and resources for forensic use of SNPs in individual identification. Forensic Sci Int Genet. 2012; 6(5):646-52.

The invention claimed is:

1. An in-vitro or ex-vivo method of monitoring the status of a transplanted organ in a subject, comprising:
   a) providing cell-free DNA from a biological sample obtained from a subject who is the recipient of an organ transplant from a donor;
   b) amplifying DNA regions in the cell-free DNA in a multiplex reaction utilizing 270 nucleic acid primers, wherein the nucleic acid primers are SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, and wherein the nucleic acid primers are the reverse complement of SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270;
   c) sequencing a panel of 94 single nucleotide polymorphisms (SNPs) from the cell-free DNA amplified in step b), and
   d) calculating the percentage of donor-derived cell-free DNA in the biological sample using the formula:

$DFi\% = (AF(SNPi) - AF(SNPirec))/(AF(SNPidon) - AF(SNPirec))$ times 100 for each SNPi; and total DF % is calculated as: DF % = mean $DFi\% \pm SD\ DFi$;
   wherein AF(SNPi) is the allele frequency of the SNP considered, calculated for the total cfDNA mixture (donor+recipient), and AF(SNPidon) and AF(SNPirec) is the allele frequency of the SNP considered in the donor and recipient cell-free DNA respectively, according to their genotype; and
wherein the status of the transplanted organ in the subject is detected by evaluating the percentage of the donor-derived cell-free DNA with respect to the recipient cell-free DNA, using the recipient genomic DNA as reference.

2. The method of claim 1, wherein calculating the quantity of the donor-derived cell-free DNA at step d) comprises calculating the differences in SNP positions by identifying and comparing variations in specific nucleotide positions between the donor-derived cell-free DNA and the recipient-derived cell-free DNA, using the recipient genomic DNA previously characterized, as reference.

3. The method of claim 1, wherein the transplanted organ is selected from heart, lung, kidney, liver and pancreas.

4. The method of claim 1, wherein a change in the percentage of the donor-derived cell-free DNA during a period of time is indicative of the status of the transplanted organ.

5. The method of claim 4, wherein an increase in the percentage of donor-derived cell-free DNA over a time interval is indicative of transplant rejection, a need for adjusting immunosuppressive therapy, and/or a need for further investigation of the transplanted organ status.

6. The method of claim 4, wherein a decrease in the percentage of the donor-derived cell-free DNA over the time interval is indicative of transplant tolerance, a need for adjusting immunosuppressive therapy, and/or a need for further investigation of the transplanted organ status.

7. The method of claim 4, wherein a value under 5% or no change in the percentage of the donor-derived cell-free DNA over the time interval is indicative of stable transplant rejection status and/or opportunity for adjusting immunosuppressive therapy.

8. The method of claim 1, wherein the biological sample is taken from a transplant recipient within days after, weeks after, about three months after, about six months after, about nine months after, or less than one year after the transplant event.

9. The method of claim 1, wherein the method is repeated with biological samples taken for one to three consecutive months, starting at the one year anniversary of the transplant event with samples being collected about every two weeks.

10. The method of claim 1, wherein the 94 single nucleotide polymorphisms sequenced at step c) are rs1005533, rs10092491, rs1015250, rs1024116, rs1028528, rs1031825, rs10488710, rs10495407, rs1058083, rs10773760, rs1109037, rs1294331, rs12997453, rs13182883, rs13218440, rs1335873, rs1336071, rs1355366, rs1357617, rs1360288, rs1382387, rs1413212, rs1454361, rs1463729, rs1490413, rs1493232, rs1498553, rs1523537, rs1528460, rs159606, rs1736442, rs1821380, rs1886510, rs1979255, rs2040411, rs2046361, rs2056277, rs2076848, rs2107612, rs2111980, rs214955, rs221956, rs2269355, rs2342747, rs2399332, rs251934, rs279844, rs2830795, rs2831700, rs2920816, rs321198, rs338882, rs354439, rs3780962, rs430046, rs4364205, rs445251, rs4530059, rs4606077, rs560681, rs576261, rs6444724, rs6811238, rs6955448, rs7041158, rs717302, rs719366, rs722098, rs722290, rs727811, rs729172, rs733164, rs735155, rs737681, rs740598, rs740910, rs763869, rs8037429, rs8078417, rs826472, rs873196, rs876724, rs891700, rs901398, rs907100, rs914165, rs917118, rs938283, rs96468, rs987640, rs9905977, rs993934, rs9951171, or rs10776839.

* * * * *